United States Patent
Ishihara et al.

(10) Patent No.: US 10,617,392 B2
(45) Date of Patent: Apr. 14, 2020

(54) ULTRASOUND IMAGING DEVICE AND ULTRASOUND IMAGING METHOD

(71) Applicant: Hitachi, Ltd., Tokyo (JP)

(72) Inventors: Chizue Ishihara, Tokyo (JP); Hiroki Tanaka, Tokyo (JP); Kunio Hashiba, Tokyo (JP); Hiroshi Kuribara, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 729 days.

(21) Appl. No.: 14/762,895

(22) PCT Filed: Jan. 31, 2014

(86) PCT No.: PCT/JP2014/052315
§ 371 (c)(1),
(2) Date: Jul. 23, 2015

(87) PCT Pub. No.: WO2014/119746
PCT Pub. Date: Aug. 7, 2014

(65) Prior Publication Data
US 2015/0351723 A1 Dec. 10, 2015

(30) Foreign Application Priority Data

Feb. 4, 2013 (JP) ................................. 2013-019787

(51) Int. Cl.
*G01S 7/52* (2006.01)
*A61B 8/08* (2006.01)
(Continued)

(52) U.S. Cl.
CPC ............ *A61B 8/5207* (2013.01); *A61B 8/145* (2013.01); *A61B 8/4483* (2013.01); *A61B 8/54* (2013.01);
(Continued)

(58) Field of Classification Search
None
See application file for complete search history.

(56) References Cited

U.S. PATENT DOCUMENTS

| 5,377,682 A | * | 1/1995 | Ueno | ........................ | A61B 8/12 |
| | | | | | 600/446 |
| 5,577,505 A | | 11/1996 | Brock-Fisher et al. | | |

(Continued)

FOREIGN PATENT DOCUMENTS

| JP | 61-279235 A | 12/1986 |
| JP | 2000-300564 A | 10/2000 |

(Continued)

OTHER PUBLICATIONS

C. Ishihara et al., Tissue Harmonic Imaging Based on Amplitude Modulation by Controlling Number of Driving Elements, IEEE International Ultrasonics Symposium Proceedings, 2012, pp. 378-381.

(Continued)

*Primary Examiner* — Angela M Hoffa
*Assistant Examiner* — Farouk A Bruce
(74) *Attorney, Agent, or Firm* — Mattingly & Malur, PC

(57) ABSTRACT

There is provided a technique for obtaining a high-quality image by extracting only a nonlinear component with high accuracy in ultrasonic imaging using an amplitude modulation method of THI. By removing a fundamental wave component with high accuracy by making the influence of electrical distortion due to analog amplification on the echo signals of ultrasonic waves having different sound pressure levels approximately the same, only the nonlinear component is extracted with high accuracy. For example, the above influence is made to be the same by controlling the ampli- (Continued)

fication factor of an amplification section. In addition, the above influence is made to be the same by restoring the digital data with a filter.

14 Claims, 11 Drawing Sheets

(51) Int. Cl.
*A61B 8/14* (2006.01)
*A61B 8/00* (2006.01)
*G01S 15/89* (2006.01)

(52) U.S. Cl.
CPC ........ *G01S 7/5202* (2013.01); *G01S 7/52033* (2013.01); *G01S 7/52038* (2013.01); *G01S 15/8915* (2013.01); *G01S 15/8927* (2013.01)

(56) References Cited

U.S. PATENT DOCUMENTS

| | | | |
|---|---|---|---|
| 8,454,517 B2 | 6/2013 | Sato | |
| 2002/0147398 A1 | 10/2002 | Kawagishi et al. | |
| 2003/0058043 A1* | 3/2003 | Yonenaga | H03F 1/3235 330/52 |
| 2005/0256404 A1* | 11/2005 | Sato | A61B 8/481 600/437 |
| 2006/0173308 A1* | 8/2006 | Sasaki | A61B 8/00 600/437 |
| 2009/0028578 A1* | 1/2009 | Sun | H04B 10/25137 398/193 |
| 2010/0324418 A1* | 12/2010 | El-Aklouk | G01S 7/5208 600/441 |

FOREIGN PATENT DOCUMENTS

| | | |
|---|---|---|
| JP | 2001-286456 A | 10/2001 |
| JP | 2001-286466 A | 10/2001 |
| JP | 2001-353155 A | 12/2001 |
| JP | 2004-208918 A | 7/2004 |
| JP | 2005-319177 A | 11/2005 |
| JP | 2006-149502 A | 6/2006 |
| JP | 2013-000351 A | 1/2013 |

OTHER PUBLICATIONS

Chizue Ishihara et al., Amplitude modulation with temporal control of Number of driving elements for tissue harmonic imaging, Procceding of Symposium on Ultrasonic Electronics Koen Ronbunshu, Nov. 2011, pp. 145 to 146, vol. 32.
International Search Report of PCT/JP2014/052315.
International Preliminary Report on Patentability received in corresponding International Application No. PCT/JP2014/052315 dated Aug. 13, 2015.
Japanese Office Action received in corresponding Japanese Application No. 2014-559783 dated Jul. 26, 2016.
Extended European Search Report received in corresponding European Application No. 14746526.4 dated Sep. 6, 2016.
Communication Pursuant to Article 94(3) EPC received in corresponding European Application No. 14 746 526.4 dated Oct. 12, 2018.

* cited by examiner

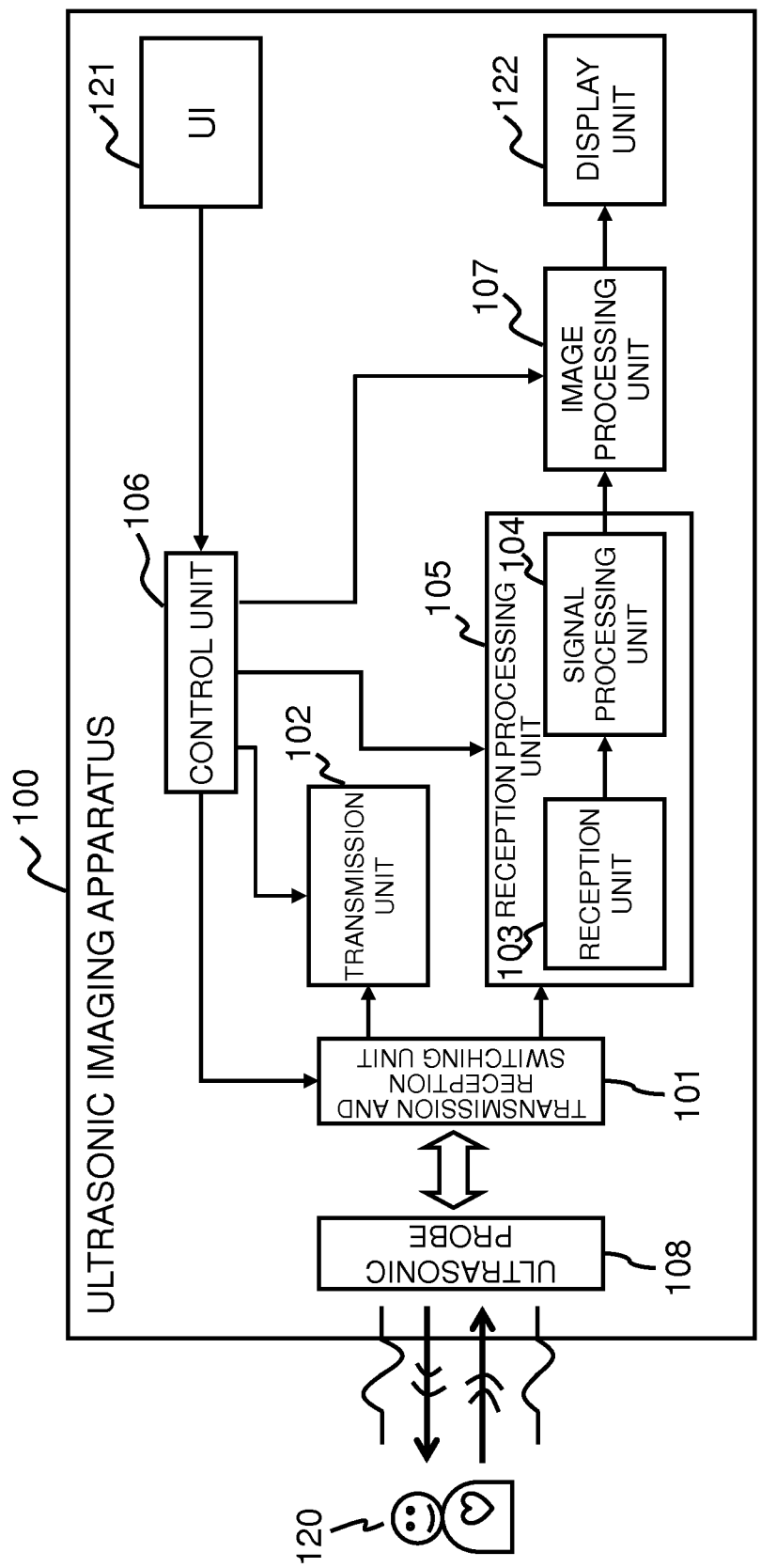

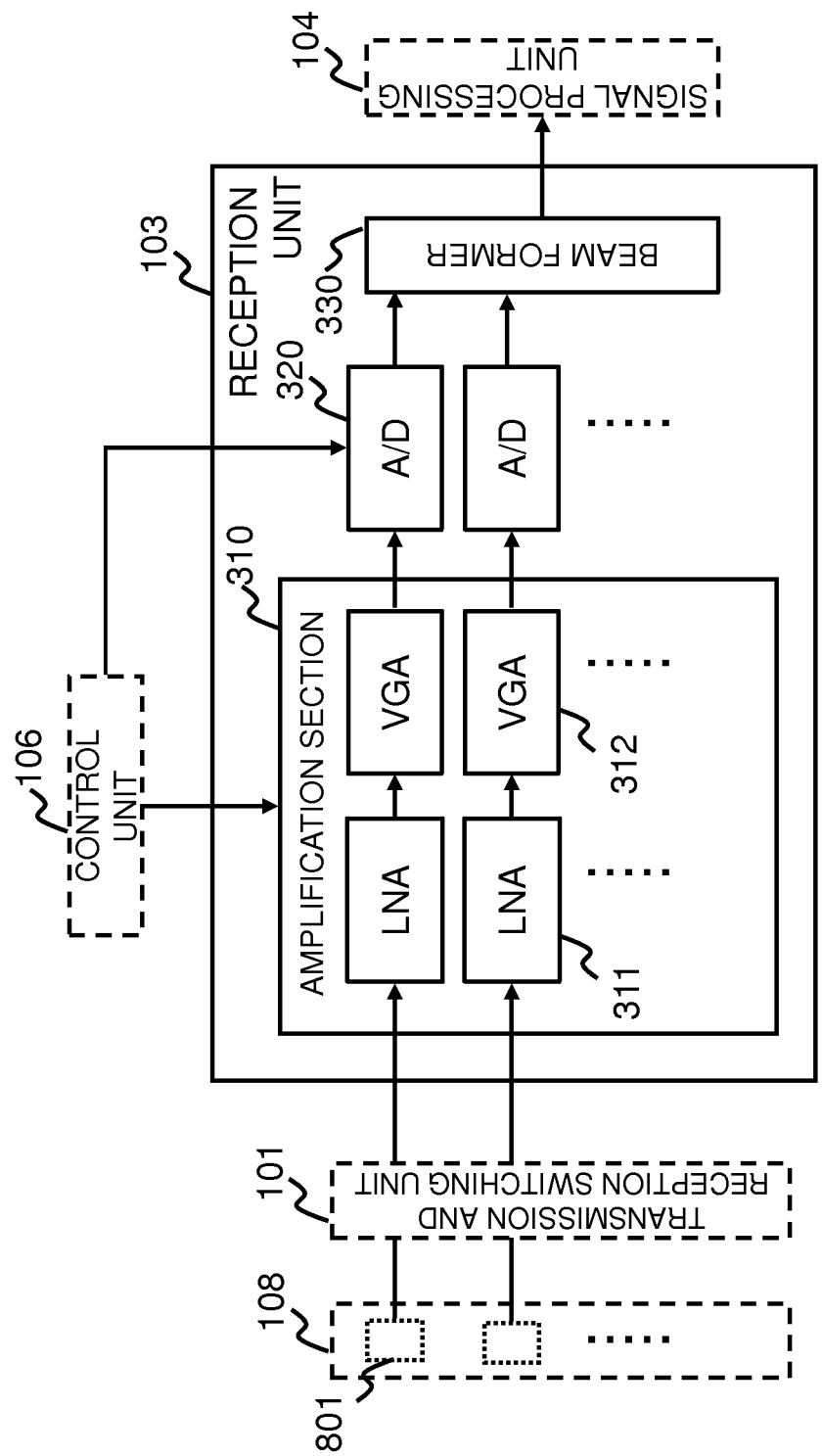

ULTRASOUND IMAGING DEVICE AND ULTRASOUND IMAGING METHOD

TECHNICAL FIELD

The present invention relates to an imaging technique in an ultrasonic imaging apparatus, and in particular, to a nonlinear imaging technique.

BACKGROUND ART

In imaging using an ultrasonic wave, image data and time-series data are generated based on the reflected wave (echo) of an ultrasonic wave emitted to an object. Since ultrasonic waves are partially reflected on a boundary where the acoustic impedance is different while propagating through the object, echo having amplitude depending on the impedance difference is generated. Accordingly, the boundary surface can be displayed as a tomographic image of the object. In this case, waveform distortion occurs due to the characteristics that the ultrasonic wave propagates faster in a portion with high sound pressure and propagates slowly in a portion with low sound pressure.

Due to this waveform distortion, a nonlinear component formed of a harmonic or a difference frequency is generated in addition to the fundamental wave component of the emitted acoustic wave. Compared with a normal imaging method in which all echoes including the fundamental wave component are used for imaging, when only the nonlinear component is used for imaging, it is possible to more emphasize the difference between light and shade in the image. Therefore, it is possible to obtain a high-resolution image. Such imaging for imaging the nonlinear component of the body tissue is called tissue harmonic imaging (THI).

In the THI, as a method of extracting the nonlinear component from the echo, there is a method called an amplitude modulation method (for example, refer to PTL 1). In general, the fundamental wave component is proportional to the amplitude, and the nonlinear component generated as a waveform distortion component is proportional to the square of the amplitude of the transmitted fundamental wave sound pressure. The amplitude modulation method is a method of canceling the fundamental wave component using this. Specifically, the sound pressure level (amplitude) of the second transmission is set to 1/k (k is an integer of 1 or more) of the first transmission, and the echo is multiplied by k and the result is subtracted from the echo of the first transmission, thereby obtaining a reception signal (reception beam) excluding the fundamental wave component.

CITATION LIST

Patent Literature

PTL 1: JP-A-2001-353155

SUMMARY OF INVENTION

Technical Problem

In the amplitude modulation method, as described above, two types of ultrasonic waves having the same waveform and different sound pressure levels (amplitudes) (one of the sound pressure levels is k times the other sound pressure level) are transmitted, echoes of the two ultrasonic waves are received, and the nonlinear component is extracted by arithmetic processing. Before the arithmetic processing, each is converted into an electrical signal (echo signal), and is amplified by a pre-amplifier or the like in an analog circuit. In general, in the amplifier, a range in which the linearity of the output voltage with respect to the input voltage (linear range) can be maintained is limited. Accordingly, when an input signal with a voltage larger than the linear range passes through the pre-amplifier, the waveform of the output signal is distorted or saturated (clipped).

Therefore, when the amplitude modulation method is used, only the echo obtained corresponding to the ultrasonic wave having larger amplitude may exceed the linear range of the amplifier, and the waveform may be distorted or clipped. When the echoes have such electrical distortion at the analog circuit, the amplitude ratio of two echo signals after passing through the pre-amplifier is not the same as the amplitude ratio at the time of transmission. In subsequent arithmetic processing of the amplitude modulation method, a calculation is performed on the assumption that the amplitude ratio of two reception signals is the same as an amplitude ratio at the time of transmission. Therefore, since it is not possible to perform a calculation correctly, it is not possible to extract a nonlinear component with high accuracy from the reception beam finally (echo signal) obtained.

The present invention has been made in view of the aforementioned situation, and it is an object of the present invention to provide a technique for obtaining a high-quality image by extracting only a nonlinear component with high accuracy in ultrasonic imaging using the amplitude modulation method of the THI.

Solution to Problem

In the amplitude modulation method of the THI of ultrasonic imaging, the influence of electrical distortion of the signal waveform to the two echo signals having different sound pressure levels due to analog amplification are formed to be approximately equal to each other. And then, a nonlinear component is extracted with high accuracy According to an aspect of the invention, there is provided an ultrasonic imaging apparatus, including: a transmission unit that transmits an ultrasonic beam multiple times to a predetermined position of an imaging target through an ultrasonic probe; a reception processing unit that receives an echo of the ultrasonic beam from the imaging target through the ultrasonic probe in a channel unit set in advance and extracts a nonlinear component after analog amplification; an image processing unit that constructs an image of the imaging target using the nonlinear component; and a control unit that controls the reception processing unit and the transmission unit. The multiple transmissions include one non-modulated transmission in which the ultrasonic beam is transmitted with a predetermined set amplitude, and the control unit controls the reception processing unit such that an influence on an echo due to the analog amplification is approximately the same between an echo of the non-modulated transmission and an echo of modulated transmission that is a transmission other than the non-modulated transmission.

According to another aspect of the invention, there is provided an ultrasonic imaging method, including: obtaining echoes by performing one non-modulated transmission for transmitting an ultrasonic beam to a predetermined position of an imaging target with a set amplitude that is set in advance and one or more modulated transmissions for transmitting the ultrasonic beam with an amplitude obtained by modulating the set amplitude; making an influence of electrical distortion due to analog amplification approximately the same between the echo of the non-modulated transmission and the echo of the modulated transmission; extracting a nonlinear component from the obtained result; and constructing an image of the imaging target from the extracted nonlinear component.

Advantageous Effects of Invention

In the ultrasonic imaging using the amplitude modulation method of the THI, it is possible to obtain a high-quality image by extracting only a nonlinear component with high accuracy.

BRIEF DESCRIPTION OF DRAWINGS

FIG. 1 is a block diagram showing the overall configuration of an ultrasonic imaging apparatus of a first embodiment.

FIG. 3 is a block diagram of a reception unit of the first embodiment.

DESCRIPTION OF EMBODIMENTS

First Embodiment

Figure 2A:
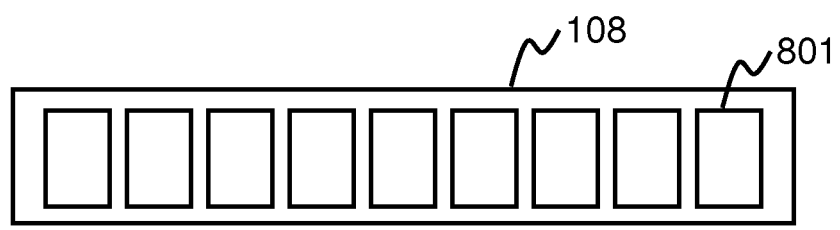
FIG. 2A is a diagram for explaining an ultrasonic probe 108 of the first embodiment.

A first embodiment to which the present invention is applied will be described. Hereinafter, in all diagrams for explaining respective embodiments, components having the same functions are basically denoted by the same reference numerals unless otherwise specified, and repeated explanation thereof will be omitted.

First, the overall configuration of an ultrasonic imaging apparatus 100 of the present embodiment will be described. FIG. 1 is a block diagram showing the schematic configuration of the ultrasonic imaging apparatus 100 of the present embodiment. The ultrasonic imaging apparatus 100 of the present embodiment includes a transmission and reception switching unit 101, a transmission unit (transmission beamformer) 102, a reception processing unit 105, an image processing unit 107, and an ultrasonic probe 108. In addition, the ultrasonic imaging apparatus 100 further includes a user interface (UI) 121 as an interface for receiving an instruction from the user and the input of various parameters and a display unit 122 for displaying a processing result.

The ultrasonic probe 108 includes multiple electro-acoustic transducer elements (transducers) having a function of converting an electrical signal into acoustic waves and acoustic waves into an electrical signal. These electro-acoustic transducer elements form an ultrasonic transmission and reception surface by being arrayed in a one-dimensional or two-dimensional manner in a predetermined arrangement in the ultrasonic probe 108. The ultrasonic probe 108 is formed in an external shape suitable for being used with the ultrasonic transmission and reception surface in contact with an imaging target 120.

The multiple arrayed electro-acoustic transducer elements are virtually or physically divided into multiple channels 801 set in advance, as shown in FIG. 2A. Each channel 801 is formed by one or multiple electro-acoustic transducer elements.

The transmission unit 102 transmits a transmission signal to multiple electro-acoustic transducer elements of the ultrasonic probe 108 to drive those elements in units of the channel 801, thereby transmitting an ultrasonic beam to a predetermined position of the imaging target 120. In response to an instruction from a control unit 106, the transmission unit 102 determines a waveform type and delay time, amplitude modulation, weighting, and the like for each channel 801, generates a transmission waveform (transmission signal), and transmits the transmission waveform to the transmission and reception switching unit 101. The control unit 106 transmits the instruction according to parameters (transmission frequency, wavenumber, transmission focus position, amplitude, and the like) received from the user through the UI 121.

Then, a transmission signal having a delay time matched with a transmission focus is output from the transmission unit 102 for each channel 801, and is transmitted to the electro-acoustic transducer element, which forms each channel 801 of the ultrasonic probe 108, through the transmission and reception switching unit 101.

Each electro-acoustic transducer element converts the transmission signal into acoustic waves. By emitting acoustic waves (transmission pulses) from each electro-acoustic transducer element, a sound field (an ultrasonic beam or a transmission beam) focused at a focal position set by the user is formed.

In the present embodiment, the amplitude modulation method of the THI is realized. Therefore, the transmission unit 102 of the present embodiment transmits ultrasonic beams, which have the same waveform and different sound pressure levels (amplitudes), multiple times to the predetermined position of the imaging target through the ultrasonic probe 108.

The echo of the ultrasonic beam (transmission beam) reflected from the imaging target 120 is received by each electro-acoustic transducer element of the ultrasonic probe 108, and is converted into an electrical signal (reception signal). The reception signal of each electro-acoustic transducer element is transmitted to the reception processing unit 105 through the transmission and reception switching unit 101.

The reception processing unit 105 receives the echo of the ultrasonic beam from the imaging target 120, in units of the channel 801 set in advance, through the ultrasonic probe 108, obtains digital data by digitally converting the reception signal after analog amplification, and extracts a nonlinear component included in the obtained digital data.

As shown in FIG. 1, the reception processing unit 105 of the present embodiment includes a reception unit (reception beamformer) 103 that obtains a reception beam by performing beam forming the digital data from each channel 801 and a signal processing unit 104 that performs arithmetic processing on the reception beam to extract a nonlinear component.

The reception unit 103 performs analog signal processing on the reception signal received by the multiple electro-acoustic elements of the ultrasonic probe 108, and then performs digital conversion to generate a reception beam. In the analog signal processing, signal amplification is performed. Therefore, as shown in FIG. 3, the reception unit 103 includes an analog circuit (amplification section) 310 that performs analog amplification (or attenuation) of the received echo, an analog-to-digital conversion circuit (analog-to-digital conversion section; A/D conversion section) 320 that converts the echo after analog amplification into digital data, and a beam former 330. The beam former 330 generates a reception beam by adding the digital data of each channel 801 after applying the delay time corresponding to the focus point thereto.

In the present embodiment, the amplification section 310 and the A/D conversion section 320 are provided for each channel of the ultrasonic probe 108. In the amplification section 310, for example, amplifiers, such as an LNA 311 and a VGA 312, are provided. The amplification factor of each amplifier provided in the amplification section 310 is controlled by a control signal from the control unit 106. In the amplification section 310, for example, only while a control signal for changing to a predetermined amplification factor is being received from the control unit 106, the amplification factor is changed to a amplification factor designated by the control signal.

Figure 2B:
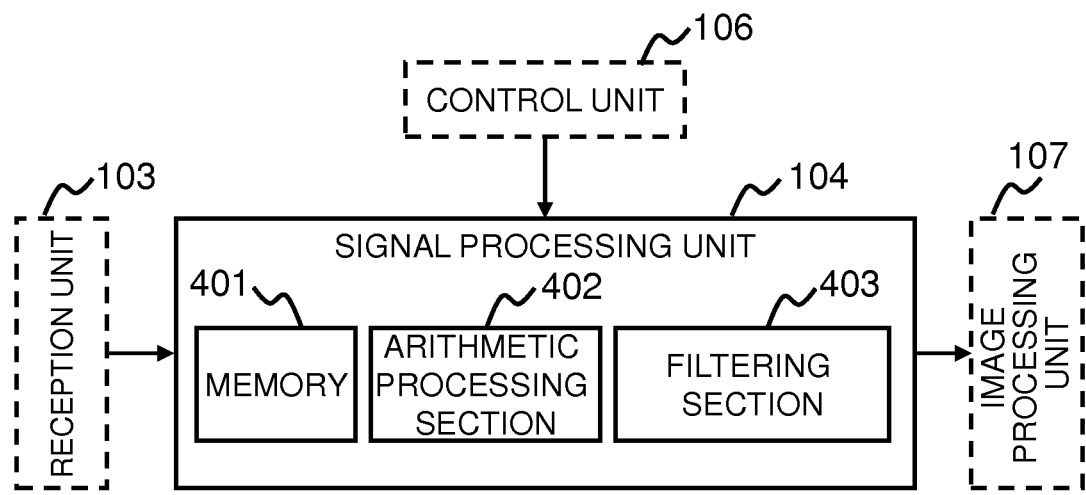
FIG. 2B is a block diagram of a signal processing unit of the first embodiment.

The signal processing unit 104 performs amplification processing, filtering processing, and signal arithmetic processing on the signal (reception beam) received from the reception unit 103. Therefore, as shown in FIG. 2B, the signal processing unit 104 includes a memory 401, an arithmetic processing section 402 that performs arithmetic processing on a signal, and a filtering section 403 that performs filtering processing. The amplification processing is performed according to time gain compensation (TGC), a amplification factor, or the like set by the user through the user interface 121. If necessary, the reception beam is temporarily stored in the memory 401. An output from the signal processing unit 104 is transmitted to the image processing unit 107.

The image processing unit 107 constructs image data and time-series data using a nonlinear component that is output from the signal processing unit 104. The constructed image data and time-series data are output to the display unit 122 so as to be displayed thereon.

The control unit 106 controls the operations of the transmission unit 102, the reception processing unit 105, and the image processing unit 107. In the present embodiment, the control unit 106 controls the operations by transmitting a control signal to each of the units, thereby realizing the THI. Details of the control performed by the control unit 106 of the present embodiment will be described later.

The control unit 106 includes a CPU, a memory, and a storage device, and each of the functions described above is realized when the CPU loads a program stored in the storage device to the memory and executes it.

Other components of the ultrasonic imaging apparatus 100 excluding the ultrasonic probe 108 can also be mounted in a separate housing from the ultrasonic probe 108 as a main unit. Some of the component can be disposed in the ultrasonic probe 108.

Prior to explanation of the control performed by the control unit 106 of the present embodiment, the amplitude modulation method of the THI realized by the ultrasonic imaging apparatus 100 of the present embodiment will be described.

In the amplitude modulation method, the transmission of an ultrasonic beam to the same imaging part is performed multiple times, the echo (reception signal) of each transmission is stored, and image data of a predetermined imaging region is generated by the stored reception signals. Hereinafter, a case in which the number of transmissions is 2 times will be described as an example.

Figure 4A:
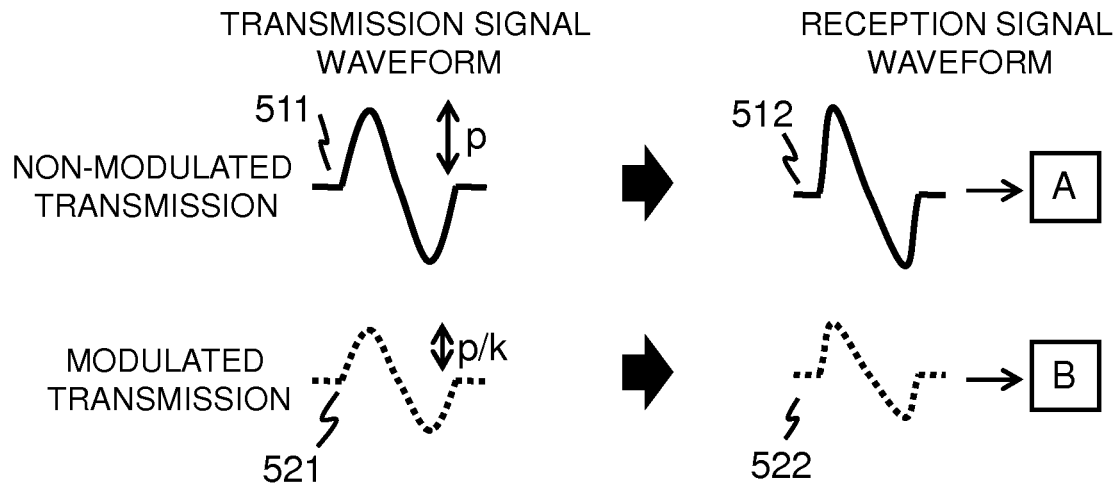
FIG. 4A is a diagram for explaining the THI based on the amplitude modulation method at the time of two transmissions.
Figure 4B:
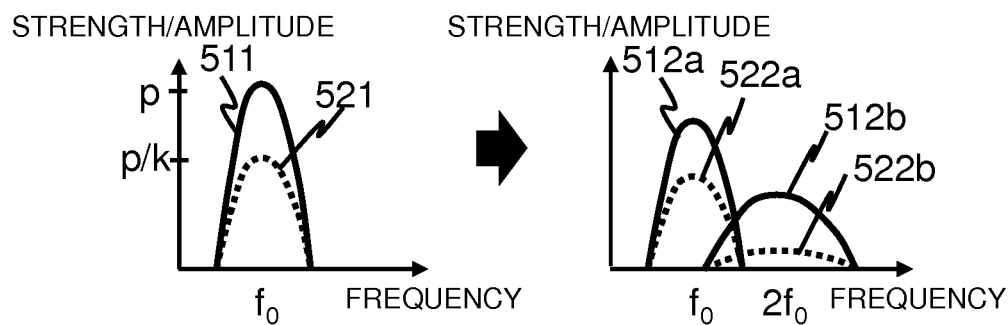
FIG. 4B is a diagram for explaining the THI based on the amplitude modulation method at the time of two transmissions.

In the amplitude modulation method, as shown in FIGS. 4A and 4B, in the first transmission, the amplitude of a transmission signal 511 is set to a predetermined amplitude (set amplitude) p, and the ultrasonic beam is transmitted. In the second transmission, the amplitude of the transmission signal 521 is modulated to $1/k$ (k is a real number satisfying $k>1$) times the set amplitude p, and the ultrasonic beam is transmitted. Hereinafter, the transmission in which the amplitude of the transmission signal is the set amplitude p (first transmission) is called non-modulated transmission, and the transmission in which the amplitude of the transmission signal is set by modulating the set amplitude (second transmission) is called modulated transmission. In addition, $1/k$ is the amplitude ratio of the ultrasonic beam generated from a transmission signal 521 at the time of modulated transmission to the ultrasonic beam generated from the transmission signal 511 at the time of non-modulated transmission. k is also referred to as a modulation coefficient.

Reception signals (echoes) obtained by the respective transmissions are assumed to be a non-modulated reception signal 512 and a modulated reception signal 522. The center frequency of the fundamental wave component of the transmission signal is set to $f_0$. In this case, the main center frequency of the nonlinear component is $2f_0$.

The nonlinear component is generated in proportion to the square of the sound pressure level (amplitude) of the echo. Therefore, as shown in FIG. 4B, the amplitude of a nonlinear component 522b of the modulated reception signal 522 is $1/k^2$ of the amplitude p of a nonlinear component 512b of the non-modulated reception signal 512, and the generation rate of the nonlinear component from the modulated reception signal 522 is smaller than the generation rate from the non-modulated reception signal 512. From the law of energy conservation, the energy of fundamental wave band components 512a and 522a that are original signal components decreases according to the generated nonlinear components 522b and 512b.

In the amplitude modulation method, the arithmetic processing section 402 performs multiplication processing for multiplying a modulation coefficient k so that the energy of the modulated reception signal 522 matches the energy of the non-modulated reception signal 512, subtracts the result from the non-modulated reception signal 512, and extracts an acoustic distortion component (THI signal) configured to mainly include a nonlinear component.

Figure 4C:
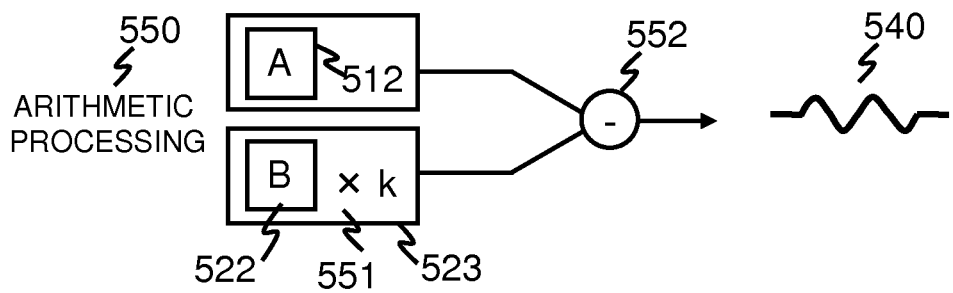
FIG. 4C is a diagram for explaining the THI based on the amplitude modulation method at the time of two transmissions.

Specifically, an acoustic distortion component (THI signal) 540 configured to mainly include a nonlinear component is extracted by performing arithmetic processing 550 shown in FIG. 4C. In the arithmetic processing 550, multiplication processing 551 for multiplying the modulated reception signal 522 by k is performed to generate a signal 523 having numerically the same energy as the non-modulated reception signal 512. Then, subtraction processing 552 for subtracting the generated signal 523 from the non-modulated reception signal 512 is performed.

Figure 4D:
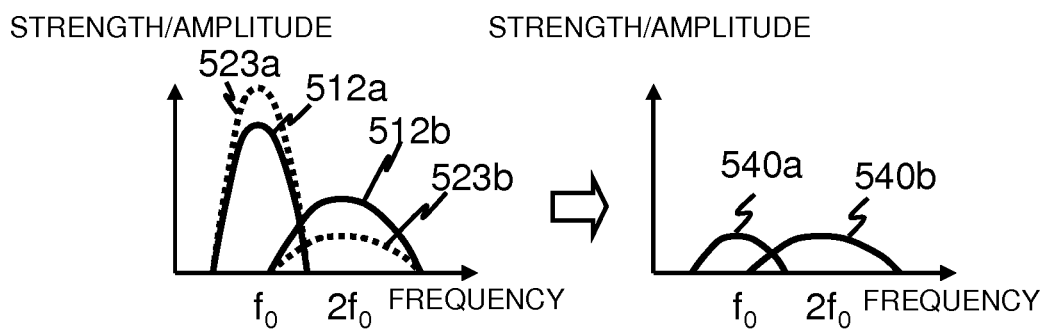
FIG. 4D is a diagram for explaining the THI based on the amplitude modulation method at the time of two transmissions.

In addition, as shown in FIG. 4D, a fundamental wave band component 523a and a nonlinear component 523b of the signal 523 are different from the fundamental wave band component 512a and the nonlinear component 512b of the non-modulated reception signal 512. Both the differences in the two bands are caused by nonlinear propagation. By the subtraction processing 552, not only a difference between nonlinear components 540b but also a difference between fundamental wave band components 540a is obtained as the acoustic distortion component (THI signal) 540. This acoustic distortion component (THI signal) 540 is a component proportional to the square of the sound pressure amplitude p of the transmission acoustic wave, and constructs an image from the THI signal to realize the THI.

In the arithmetic processing 550, the multiplication processing 551 may be set to multiply the non-modulated reception signal 512 by 1/k.

In general, the arithmetic processing 550 is performed on digital data obtained by digital conversion after analog amplification in the analog amplifier. However, the dynamic range (linear amplification range) of the analog amplifier in which the linearity of the output signal to the input signal is maintained is limited. When the voltage amplitude of the input signal deviates from the linear amplification range of each analog amplifier, the amount of amplification or the phase characteristic of the output signal is deformed. This distorts the waveform of the output signal, or causes saturation (clip).

When the amplitude p of the non-modulated transmission signal is greatly different from the amplitude p/k of the modulated transmission signal, only the waveform of the non-modulated reception signal 512 that is a high-amplitude reception signal is greatly distorted. And the high-amplitude reception signal becomes to have a different amplitude that is assumed. Accordingly, the amplitude ratio between the non-modulated reception signal 512 and the modulated reception signal 522 after passing through the analog amplifier is also different from the amplitude ratio (1/k) before passing through the analog amplifier. Since the arithmetic processing 550 is performed on the assumption that the non-modulated reception signal 512 is an amplitude ratio (1/k) at the time of transmission, it is not possible to correctly perform the calculation if the amplitude ratio is different from the assumption.

For example, assuming that the amplification factor of the amplification section 310 is G, if both the amplitude p of the non-modulated reception signal 512 and the amplitude p/k of the modulated reception signal 522 are in the linear amplification range of the amplification section 310, the amplitudes of the respective output signals are p*G and p*G/k. On the other hand, when the amplitude p of the non-modulated reception signal 512 is over the linear amplification range or reaches the output limit of the amplification section 310, the signal waveform of the output from the amplification section 310 is distorted or clipped. Accordingly, the amplitude of the output signal from the amplification section 310 of the non-modulated reception signal 512 becomes smaller than the assumption. That is, the amplitude of the non-modulated reception signal 512 after passing through the amplification section 310 is smaller than p*G. Therefore, the amplitude ratio of two signals obtained after passing through the amplification section 310 is not 1/k.

In such a case, when the arithmetic processing 550 shown in FIG. 4C is performed, it is not possible to extract only the distortion component (THI signal) 540 of the acoustic wave in the nonlinear propagation. Accordingly, an electrical distortion signal that is not relevant to the THI signal remains.

In the present embodiment, in order to avoid this, the control unit 106 controls the reception processing unit 105 such that the influence of electrical distortion on the signal waveform of the reception signal (echo) due to analog amplification is approximately the same between the reception signal obtained from the echo of the non-modulated transmission and the reception signal obtained from the echo of the modulated transmission. In the present embodiment, this is realized by controlling the amplification factor of the amplification section 310.

Specifically, the control unit 106 of the present embodiment controls the amplification factor of the amplification section 310 with respect to the reception signal obtained from the echo of the modulated transmission such that the waveform distortion of the reception signal obtained from the echo of the modulated transmission after the amplification in the amplification section 310 is approximately the same as the waveform distortion of the reception signal obtained from the echo of the non-modulated transmission after the amplification in the amplification section 310.

For example, in the example shown in FIG. 4A, the amplification factor of the modulated reception signal 522 is controlled such that the waveform distortion of the modulated reception signal 522 after the amplification in the amplification section 310 is approximately the same as the waveform distortion of the non-modulated reception signal 512 after the amplification in the amplification section 310. For example, in the example shown in FIG. 4A, that is, when the amplitude of the ultrasonic beam at the time of modulated transmission is set to 1/k (k is a real number satisfying k>1) of the set amplitude p, the amplification factor at which the waveform distortions are approximately the same is k times the set amplification factor G, as described above. The set amplification factor G is an amplification factor set in the amplification section 310 in advance, and is an amplification factor of the amplification section 310 with respect to the echo of the non-modulated transmission.

This control is performed by transmitting a control signal from the control unit 106 to the amplification section 310. When no control signal is received from the control unit 106, the amplification section 310 of the present embodiment amplifies the reception signal with the set amplification factor. On the other hand, when a control signal is received from the control unit 106, the reception signal is amplified with a amplification factor according to the control signal.

In the arithmetic processing section 402 of the signal processing unit 104 of the present embodiment, only the subtraction processing 552 is performed to extract a nonlinear component. This is because the multiplication processing 551 of the arithmetic processing 550 described above is the same as processing for setting the amplification factor of the modulated reception signal 522 to k times the set amplification factor G.

In the present embodiment, in the amplification section 310, for example, the amplification factor of the VGA 312 is changed. For example, in the example shown in FIG. 4A, assuming that the amplification factor (set amplification factor) of the VGA 312 with respect to the non-modulated reception signal 512 is Gv, the amplification factor of the VGA 312 with respect to the modulated reception signal 522 is set to k*Gv times. As a result, the modulated reception signal 522 after passing through the VGA 312 becomes a signal waveform having the features of the same electrical distortion or clipping as the non-modulated reception signal 512. When the subtraction processing 552 is performed on these signals, electrical distortion components in the VGA 312 are canceled, and only the acoustic distortion component (THI signal) 540 generated during the propagation of the acoustic wave remains.

The change of the amplification factor in the amplification section 310 is not limited to the VGA 312. For example, the change of the amplification factor may also be performed in the LNA 311 connected before the VGA 312. In addition, when amplifiers other than the VGA 312 and the LNA 311 are connected, the change of the amplification factor may be performed in any of the amplifiers.

In the above, the case in which the amplitude modulation method is realized by two transmissions has been described as an example. However, the number of transmissions in the amplitude modulation method is not limited to 2 times. The number of transmissions in the amplitude modulation method may be N times (N is an integer of 3 or more). For example, assuming that the first transmission is non-modulated transmission, second and subsequent transmissions are modulated transmissions, the amplitude (set amplitude) of the non-modulated transmission is p, and the modulation coefficient of the modulated transmission that is the n-th (n is an integer of 2 or more and N or less) transmission is $k_n$ ($k_n>1$), the amplitude of the transmission signal is set to $p/k_n$. In addition, the non-modulated transmission is not limited to the first transmission.

In the arithmetic processing 550, in order to make equal the sum of the energy of the non-modulated reception signal and the energy of the modulated reception signal, the difference between the energy of the non-modulated reception signal and the energy of the modulated reception signal is calculated. Therefore, when the number of transmissions is N times, in order to make equal the sum of the energy of each modulated reception signal, processing of multiplying each modulated reception signal by the modulation coefficient $k_n$ is performed, and then the average value is calculated.

That is, assuming that the amplitude (signal strength) of the n-th reception signal is $S_n$, the multiplication processing 551 of multiplying the modulated reception signal by the modulation coefficient $k_n$ is calculated by the following equation (1). The result of the multiplication processing 551 is set to SM. In addition, the average value calculation process of the multiplication process result is calculated by the following equation (2). The result of the average value calculation process is set to SA. Assuming that the result is SS, the last subtraction processing 552 is calculated by the following equation (3).

$$SM = k_2 * S_2 + k_3 * S_3 + \ldots + k_N * S_N \quad (1)$$

$$SA = SM/(N-1) \quad (2)$$

$$SS = S_1 - SA \quad (3)$$

This SS is the acoustic distortion component (THI signal) 540 generated during the propagation of the acoustic wave.

That is, when the number of transmissions is N times, a nonlinear component is extracted by calculating the average value of digital data obtained from the echo of the modulated transmission after amplification corresponding to the modulation coefficient $k_n$ and subtracting the obtained value from the digital data obtained from the echo of the non-modulated transmission. The modulation coefficient $k_n$ is the inverse of the ratio of the amplitude of the ultrasonic beam of the modulated transmission to the set amplitude.

In addition, in the above equation (1), the modulation coefficient multiplication process may be arithmetic processing for multiplying each reception signal by $-k_n$. In this case, equation (3) becomes arithmetic processing for adding $S_1$ and SA.

Therefore, when the number of transmissions is N times, at the time of modulated transmission, the control unit 106 transmits a control signal to the amplification section 310 for each reception of the echo in order to control the amplification factor. Specifically, when amplifying the modulated reception signal having the modulation coefficient of $k_n$, a control signal is transmitted such that the amplification factor of the amplification section 310 becomes $k_n*G$. G is the set amplification factor of the amplification section 310.

The signal processing unit 104 performs only the average value calculation processing of the above equation (2) and the subtraction processing of the above equation (3).

The number of non-modulated transmissions and the modulation coefficient of the amplitude at the time of each modulated transmission are stored in a storage device provided in the control unit 106 or the like in advance. Based on this information, the control unit 106 generates the above-described control signal, and transmits the control signal to the amplification section 310.

Next, the flow of the process of the THI according to the amplitude modulation method of the present embodiment will be described. In the present embodiment, one non-modulated transmission for transmitting an ultrasonic beam to the predetermined position of the imaging target with the set amplitude that is set in advance and one or more modulated transmissions for transmitting an ultrasonic beam with an amplitude obtained by modulating the set amplitude are performed to obtain each echo, the influence of electrical distortion due to analog amplification is approximately the same between the echo of the non-modulated transmission and the echo of the modulated transmission, and a nonlinear component is extracted from the obtained result.

Figure 5:
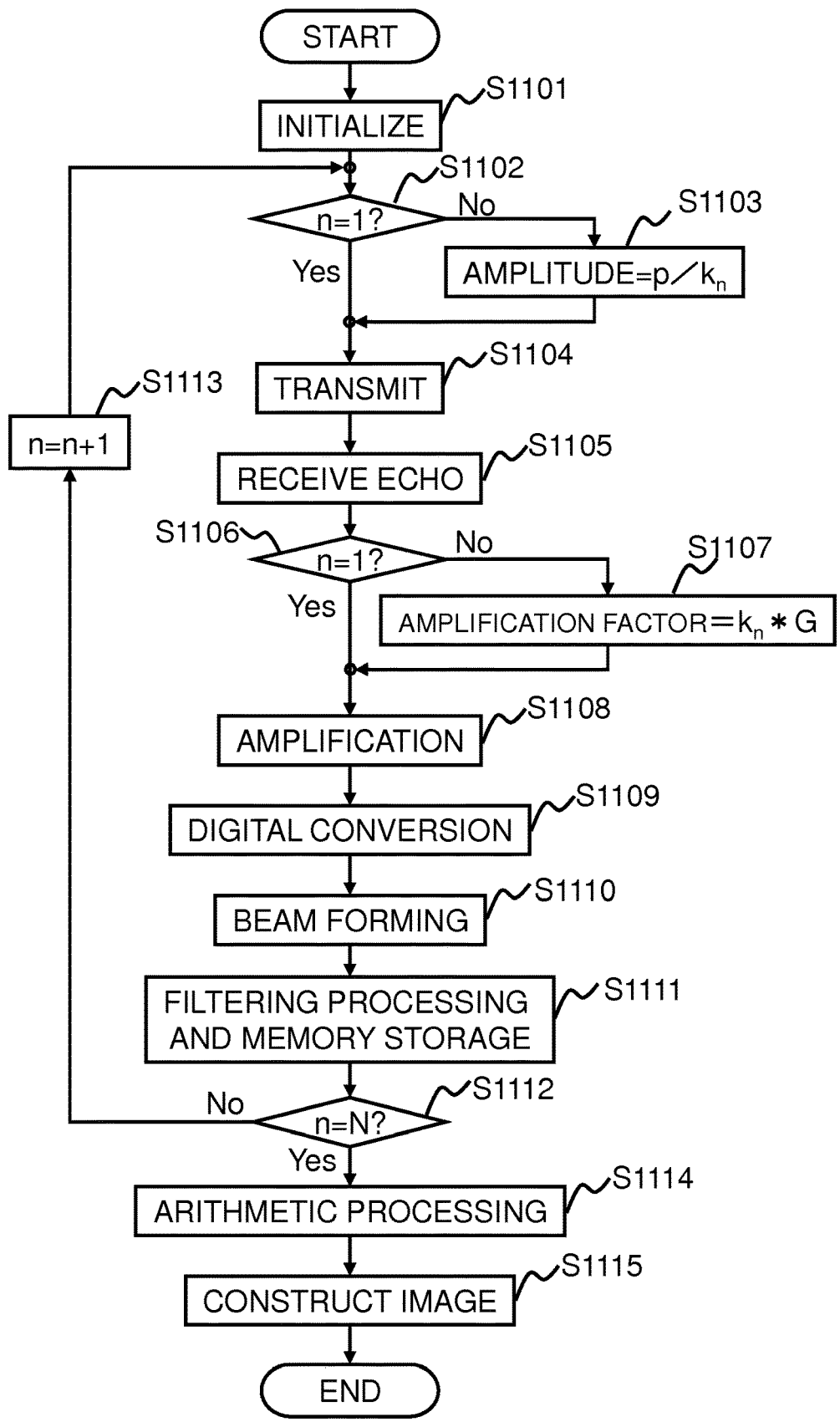
FIG. 5 is a flowchart of the THI of the first embodiment.

FIG. 5 is a process flow of the THI of the present embodiment. Here, it is assumed that the number of transmissions for creating the image data of an imaging region set in advance is N times, the amplitude of the first transmission signal is the set amplitude p, and the modulation coefficient of the n-th transmission (second or subsequent transmission) is $k_n$. That is, the amplitude of the transmission signal of the n-th transmission (second or subsequent transmission) is set to $p/k_n$. In addition, the amplification factor of the amplification section 310 is assumed to be the set amplification factor G. The set amplitude p, the coefficient $k_n$, and the set amplification factor G are determined in advance and are stored in the storage device.

First, the control unit 106 initializes each unit (step S1001). Here, n that is used as a counter is set to 1, the amplitude of the transmission signal is set to the set amplitude p, and the amplification factor of the amplification section 310 is set to the set amplification factor G.

Then, the control unit 106 determines whether or not the counter n is 1 (step S1102). If the counter n is not 1, the control unit 106 transmits a control signal to the transmission unit 102 so that the amplitude of the transmission signal is modulated to a modulation coefficient $p/k_n$ (step S1103), and the transmission unit 102 transmits an ultrasonic beam (step S1104). On the other hand, if n is 1 in step S1102, the process proceeds to step S1104 to transmit the ultrasonic beam.

When the echo is received (step S1105), the control unit 106 determines whether or not the counter n is 1 (step S1106). If the counter n is not 1, the control unit 106 transmits a control signal to the amplification section 310 in order to set the amplification factor to $k_n*G$ (step S1107), and the amplification section 310 amplifies a reception signal generated for each channel from the received echo (step S1108). On the other hand, if n is 1 in step S1106, the process proceeds to step S1108 in which the amplification section 310 amplifies the reception signal for each channel. The amplification factor at this time is the set amplification factor G.

Then, the control unit 106 causes the A/D conversion section 320 to convert the reception signal for each channel after the amplification into a digital signal (step S1109), and causes the beam former 330 to perform beam forming of the digital signal for each channel to generate a reception beam (step S1110). The control unit 106 causes the filtering section 403 to perform filtering processing, and the result is stored in the memory 401 as digital data (step S1111).

The control unit 106 repeats the process of steps S1102 to S1111 for all reception signals. That is, the process of steps S1102 to S1111 is repeated until n becomes N (steps S1112 and S1113).

After completing the above process, the control unit 106 transmits a control signal to the signal processing unit 104 so that the arithmetic processing section 402 performs arithmetic processing using the digital data stored in the memory 401 (step S1114), thereby extracting a THI signal. Then, the control unit 106 causes the image processing unit 107 to construct an image using the extracted THI signal (step S1115).

In addition, the amplitude $k_n$ of each transmission signal may differ depending on each transmission, and may be the same for the second and subsequent transmissions. In addition, the non-modulated transmission may not be the first transmission. By setting the order of the non-modulated transmission in advance, the control unit 106 performs control to use the amplification factor G of the amplification section 310 as it is only at the time of non-modulated transmission.

A process when, for example, the number of transmissions N is 3 and the respective modulation coefficients are set to $k_2=2$ and $k_3=2$ in the above flow will be specifically described. Here, it is assumed that the set amplitude is p and the set amplification factor of the amplification section 310 is G. In addition, a reception signal generated from the echo of the first transmission, a reception signal generated from the echo of the second transmission, and a reception signal generated from the echo of the third transmission are referred to as a first reception signal, a second reception signal, and a third reception signal, respectively.

In this case, the control unit 106 sets the amplification factor of the amplification section 310 to the set amplification factor G at the time of amplification of the first reception signal. On the other hand, at the time of amplification of the second and third reception signals, a control signal is output to the amplification section 310 so that the amplification factor is set to 2*G.

The A/D conversion section 320 digitally converts each reception signal after the amplification to obtain digital data. The beam former 330 performs beam forming of the obtained digital data, and then stores the result in the memory 401 as digital data. After the storage of the third reception signal into the memory 401 is completed, the arithmetic processing section 402 performs predetermined arithmetic processing using all pieces of the digital data in the memory 401.

In the amplification section 310, the second and third reception signals are amplified to twice the first reception signal. Accordingly, the sum of the, energy of the second reception signal and the energy of the third reception signal is twice the energy of the first reception signal. In order to make both the same, the above-described average value calculation processing is performed on the digital data obtained from the second reception signal and the digital data obtained from the third reception signal. Then, the result is subtracted from the digital data obtained from the first reception signal. This arithmetic processing may be arithmetic processing for multiplying the addition result of the digital data obtained from the second reception signal and the digital data obtained from the third reception signal by −½ and adding the multiplication result and the digital data obtained from the first reception signal.

In the embodiment described above, control is performed so as to increase the amplification factor at the time of amplification of the modulated reception signal. However, when all of the modulation coefficients of the modulated transmission are equally k, the amplification factor may be reduced at the time of amplification of the non-modulated reception signal. That is, the amplification factor of the modulated reception signal may be set to the set amplification factor G as it is, and the amplification factor of the non-modulated reception signal may be set to G/k.

That is, when the amplitude of the ultrasonic beam at the time of modulated transmission is 1/k times the set amplitude p, the control unit 106 controls the amplification factor of the amplification section 310 with respect to the non-modulated reception signal so as to become 1/k times the set amplification factor G. In this case, an amplification factor with respect to the modulated reception signal is assumed to be the set amplification factor G. That is, when receiving the echo of the non-modulated transmission, the control unit 106 transmits a control signal instructing a change of the amplification factor to the amplification section 310. In addition, when receiving the echo of the modulated transmission, no control signal may be transmitted.

In this case, the arithmetic processing section 402 performs subtraction processing after making equal the sum of the energy of the digital data obtained from the non-modulated reception signal and the energy of the digital data obtained from the modulated reception signal.

In the embodiment described above, one amplification section 310 is provided for each channel, and the amplification factor is changed when amplifying the modulated reception signal. However, the configuration of the amplification section 310 is not limited thereto. For example, when all of the modulation coefficients of the modulated transmission are equally k, an amplification section to be used for amplification of the non-modulated reception signal and an amplification section to be used for amplification of the modulated reception signal may be separately provided, and an amplification section to be used may be controlled by a switch or the like. In the amplification section 310, only an amplifier for changing the amplification factor may be provided for each transmission.

As described above, according to the present embodiment, in the amplitude modulation method of the THI, a nonlinear component is extracted by making the influence on the echo due to analog amplification approximately the same between the echo of the non-modulated transmission and the echo of the modulated transmission. In the present embodiment, the influence on the echo due to analog amplification is made to be approximately the same by controlling the amplification factor of the amplification section 310. For example, in the present embodiment, the amplification factor of the amplification section 310 with respect to the echo of the modulated transmission is changed. The amplification factor with respect to the echo of the modulated transmission is set such that the waveform distortion after the amplification in the amplification section 310 is approximately the same as the waveform distortion after the amplification of the non-modulated transmission. Specifically, when the amplitude of the ultrasonic beam at the time of modulated transmission is 1/k times the amplitude of the ultrasonic beam at the time of non-modulated transmission, the amplification factor with respect to the echo of the modulated transmission is set to k times the amplification factor with respect to the echo of the non-modulated transmission.

Therefore, since the waveform distortion of the non-modulated reception signal after amplification becomes approximately the same as the waveform distortion of the modulated reception signal after amplification, the amplitude ratio of both the non-modulated reception signal and the modulated reception signal after analog amplification is the same as that assumed. Based on this, it is possible to correctly perform subsequent arithmetic processing. Therefore, since it is possible to extract a nonlinear component with high accuracy, the obtained image quality is also improved.

In the ultrasonic imaging apparatus 100, it is necessary to simultaneously process the echoes of various strengths. This is because an imaging target that causes a strong echo and an imaging target that does not cause a strong echo may be simultaneously imaged and the strength of the echo changes depending on the position and angle of the imaging target with respect to the ultrasonic probe 108. For this reason, a high echo is received in some channels of the ultrasonic probe 108, while a low echo is received in other channels. In addition, whenever an imaging region changes, the strength of an echo received by the ultrasonic probe 108 changes in various ways.

However, it is difficult to secure a wide dynamic range, which can respond to all strengths that the ultrasonic imaging apparatus 100 may receive, in the analog circuit (amplifier). Therefore, it is difficult to make the reception signals of both the high echo and the low echo fall within the dynamic range of the amplifier in order to amplify both the signals with high accuracy. In particular, in order to extract the reception signal of the low echo with high accuracy, amplification of the signal amplitude in the amplifier is indispensable. Therefore, it is desirable to set the dynamic range of the amplifier to a range corresponding to the low echo signal. For this reason, in particular, the reception signal that becomes a high echo is easy to reach the outside of the dynamic range of the amplifier.

However, according to the present embodiment, even when an amplifier that does not have a wide dynamic range is used, the influence (electrical distortion or clipping) of the received waveform after amplification can be made to be the same. Therefore, it is possible to realize the high-accuracy nonlinear component extraction described above.

Second Embodiment

Next, a second embodiment to which the present invention is applied will be described. Also in the present embodiment, as in the first embodiment, the influence on the echo due to analog amplification is made to be approximately the same among all echoes by controlling the amplification factor of the amplification section. In the first embodiment, in multiple transmissions to obtain all pieces of image data, the amplification factor is changed between the modulated reception signal and the non-modulated reception signal. In the present embodiment, however, the amplification factor is changed only when the amplitude of the non-modulated reception signal deviates from the linear amplification range of the amplification section.

The configuration of the ultrasonic imaging apparatus 100 of the present embodiment is basically the same as that of the first embodiment. In the present embodiment, however, as described above, it is determined whether or not the amplitude of the non-modulated reception signal deviates from the linear amplification range of the amplification section 310. Therefore, the configuration of the reception unit 103 is different. In addition, the processes of the signal processing unit 104 and the control unit 106 are also different. The following explanation will be focused on a configuration different from the first embodiment.

Figure 6:
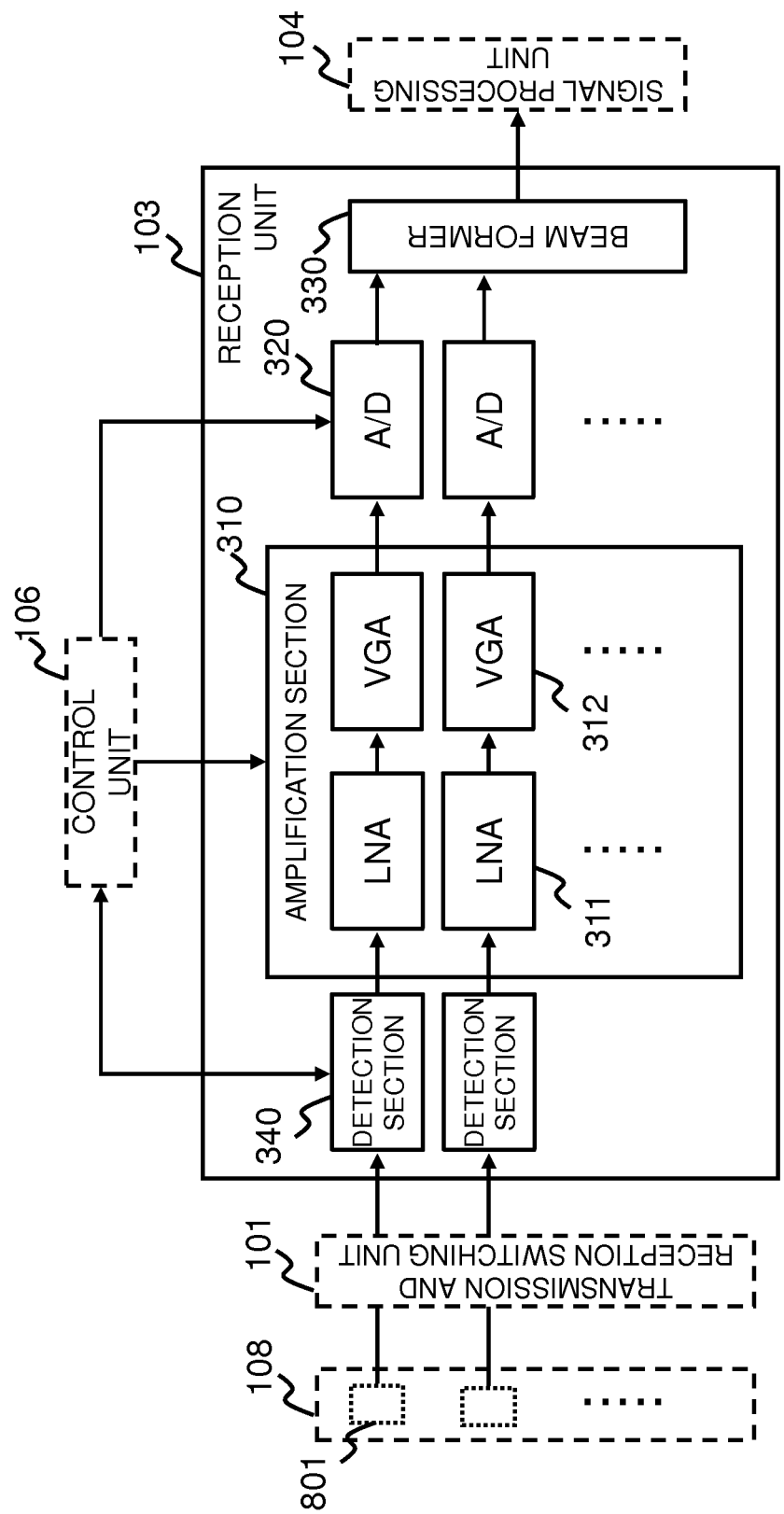
FIG. 6 is a block diagram of a reception unit of a second embodiment.

As shown in FIG. 6, the reception unit 103 of the present embodiment further includes a detection section 340 that is connected before the amplification section 310 and detects the amplitude of the reception signal (non-modulated reception signal) obtained from the echo of the non-modulated transmission. In response to the control signal from the control unit 106, the detection section 340 receives a non-modulated reception signal and detects the maximum amplitude, and notifies the control unit 106 of the result.

The control unit 106 of the present embodiment sends an instruction to detect the amplitude of the reception signal to the detection section 340, and determines whether or not to change the amplification factor of the amplification section 310 when amplifying the modulated reception signal according to the detection result. Then, only when it is determined that the amplification factor of the amplification section 310 when amplifying the modulated reception signal is changed, a control signal is transmitted to the amplification section 310. Otherwise, no control signal is transmitted to the amplification section 310. In the present embodiment, when the non-modulated reception signal deviates from the linear amplification range within the amplification section 310 or when the waveform of the output signal is distorted or clipped, it is determined that the amplification factor of the amplification section 310 when amplifying the modulated reception signal is changed.

The determination regarding whether or not to change the amplification factor of the amplification section 310 is performed according to whether or not the maximum amplitude detected by the detection section 340 exceeds a predetermined threshold value. When the maximum amplitude detected by the detection section 340 exceeds the predetermined threshold value, it is determined that the amplification factor of the amplification section 310 is changed. The threshold value is calculated in advance according to the connection order of each amplifier circuit connected within the amplification section 310 and the linear amplification range of each amplifier circuit, and is stored in the storage device of the control unit 106.

As in the first embodiment, the amplification section 310 changes the amplification factor only when a control signal is received from the control unit 106. Also in the present embodiment, as in the first embodiment, when amplifying the modulated reception signal having the modulation coefficient of $k_n$, a control signal is transmitted such that the amplification factor of the amplification section 310 becomes $k_n*G$. G is the set amplification factor of the amplification section 310.

When it is determined that the amplification factor is changed, the control unit 106 of the present embodiment transmits a control signal to the signal processing unit 104. When no control signal is received from the control unit 106, the arithmetic processing section 402 of the signal processing unit 104 performs the multiplication processing 551 of the above equation (1), the average value calculation processing of the above equation (2), and the subtraction processing 552 of the above equation (3), as the arithmetic processing 550. However, when a control signal is received from the control unit 106, the multiplication processing 551 is not performed. This is because processing equivalent to the multiplication processing 551 is performed in the preceding amplification section 310.

In addition, although the detection section 340 is disposed in the first stage of the reception unit 103 in FIG. 6, the arrangement position is not limited thereto. For example, the detection section 340 may be disposed inside the amplification section 310, or may be disposed in the later stage. The control unit 106 determines the above threshold value in advance according to the arrangement position of the detection section 340 and the data of the linear amplification range of each amplifier circuit, and stores the threshold value in the storage device or the like. In addition, an amplifier circuit itself, such as the LNA 311 or the VGA 312, may be configured to function as the detection section 340.

In the present embodiment, the amplification factor of the modulated reception signal is determined according to the amplitude of the non-modulated reception signal. For this reason, non-modulated transmission is set as the first transmission.

Next, the flow of the process of the THI according to the amplitude modulation method of the present embodiment will be described. In the present embodiment, as described above, only when the amplitude of the non-modulated reception signal exceeds the linear amplification range of the amplification section 310 that performs analog amplification, the amplification factor of the amplification section 310 when performing analog amplification of the modulated reception signal is changed.

Figure 7:
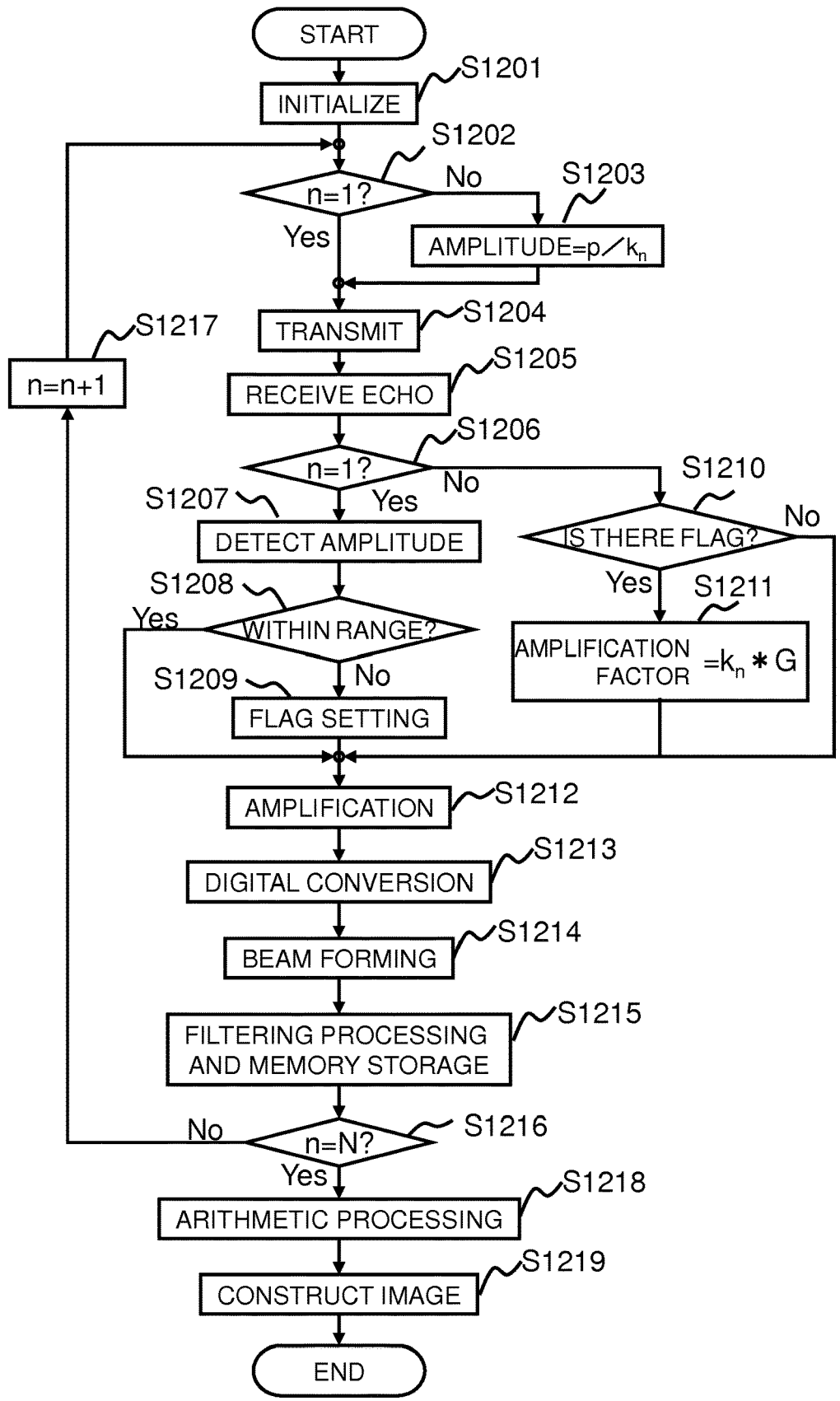
FIG. 7 is a flowchart of the THI of the second embodiment.

FIG. 7 is a process flow of the THI of the present embodiment. As in the first embodiment, it is assumed that the number of transmissions for creating the image data of an imaging region set in advance is N times, the amplitude of the first transmission signal is the set amplitude p, and the modulation coefficient of the n-th transmission (second or subsequent transmission) is $k_n$. That is, the amplitude of the transmission signal of the n-th transmission (second or subsequent transmission) is set to $p/k_n$. In addition, the amplification factor of the amplification section 310 is set to the set amplification factor G. The set amplitude p, the coefficient $k_n$, and the set amplification factor G are determined in advance and are stored in the storage device.

First, the control unit 106 initializes each unit (step S1201). Here, n that is used as a counter is set to 1, the amplitude of the transmission signal is set to the set amplitude p, and the amplification factor of the VGA 312 is set to the set amplification factor G. In the present embodiment, a flag to be described later is also initialized.

Then, the control unit 106 determines whether or not the counter n is 1 (step S1202). If the counter n is not 1, the control unit 106 transmits a control signal to the transmission unit 102 so that the amplitude of the transmission signal is modulated to a modulation coefficient $p/k_n$ (step S1203), and the transmission unit 102 transmits an ultrasonic beam (step S1204). On the other hand, if n is 1 in step S1202, the process proceeds to step S1204 directly to transmit the ultrasonic beam.

When an echo is received (step S1205), the control unit 106 determines whether or not the counter n is 1 (step S1206).

If the counter n is 1, the control unit 106 transmits a control signal to the detection section 340 so that the detection section 340 detects an amplitude, and receives the detection result (step S1207). Then, it is determined whether or not the received detection result is within the linear amplification range of the amplification section 310 by comparing the received detection result with the threshold value (step S1208). When the received detection result exceeds the threshold value, a flag is set (step S1209), and the process proceeds to the amplification processing of the amplification section 310 (step S1212). This flag is a flag that means increasing the amplification factor of the reception signal according to the modulated transmission. On the other hand, when the received detection result does not exceed the threshold value, no flag is set, and the process proceeds to the amplification processing (step S1212) directly.

If the counter n is not 1, the control unit 106 determines whether or not a flag is set (step S1210). When a flag is set, the control unit 106 transmits a control signal to the amplification section 310 so that the amplification factor becomes $k_n*G$ (step S1211), and the amplification section 310 performs amplification processing (step S1212). On the other hand, when no flag is set, a control signal to change the amplification factor is not transmitted, and the amplification processing is performed with the amplification factor G (step S1212).

Then, the control unit 106 causes the A/D conversion section 320 to convert the reception signal for each channel after the amplification into a digital signal (step S1213), and causes the beam former 330 to perform beam forming of the digital signal for each channel to generate a reception beam (step S1214). The control unit 106 causes the filtering section 403 to perform filtering processing, and the result is stored in the memory 401 as digital data (step S1215).

The control unit 106 repeats the process of steps S1202 to S1214 for all reception signals. That is, the process of steps S1202 to S1214 is repeated until n becomes N (steps S1216 and S1217).

After completing the above process, the control unit 106 causes the arithmetic processing section 402 to perform arithmetic processing using the digital data stored in the memory 401 (step S1218), thereby extracting a THI signal. In the present embodiment, when no flag is set, the arithmetic processing 550 described in the first embodiment is performed. On the other hand, when a flag is set, only the average value calculation processing and the subtraction processing 552 are performed without performing the multiplication processing 551. These are instructed by the control signal from the control unit 106. Then, the control unit 106 causes the image processing unit 107 to construct an image using the extracted THI signal (step S1219).

Also in the present embodiment, the modulation coefficient $k_n$ to determine the amplitude of the transmission signal of each modulated transmission may differ depending on each transmission, and may be the same for all transmissions.

For example, a case in which the number of transmissions is 2 times and the modulation coefficient k at the time of modulated transmission is 2 will be specifically described as an example. Here, it is assumed that the set amplitude is p and the set amplification factor of the amplification section 310 is G. In addition, a reception signal generated from the echo of the first transmission and a reception signal generated from the echo of the second transmission are referred to as a first reception signal and a second reception signal, respectively.

When the first reception signal is received, the control unit 106 causes the detection section 340 to detect the amplitude, and determines whether or not the amplitude is equal to or less than a predetermined threshold value. When the amplitude is not equal to or less than the predetermined threshold value, a flag that means changing the amplification factor when receiving the second reception signal is set. On the other hand, when the determination result indicates that the amplitude is within the range, no flag is set.

When the second reception signal is received, the control unit 106 refers to a flag. If the flag is set, the control unit 106 transmits a control signal, which instructs to set the amplification factor to 2*G, to the amplification section 310, so that the amplification section 310 performs amplification processing. Then, the arithmetic processing section 402 extracts a THI signal by subtracting the above result from the digital data generated from the first reception signal.

On the other hand, when no flag is set, a control signal is not transmitted, and the second reception signal is amplified with the amplification factor G without change. Then, the arithmetic processing section 402 extracts a THI signal by doubling the obtained digital data and subtracting the result from the digital data generated from the first reception signal.

Also in the present embodiment, when a flag is set, the arithmetic processing section 402 may be configured to multiply the digital data obtained from the second and subsequent reception signals by $-1/k_n$ and add the result and the first reception signal. In addition, when a flag is set, digital data obtained from the second and subsequent reception signals may be multiplied by −1, and the result and the first reception signal may be added.

Also in the present embodiment, when all modulation coefficients of the modulated transmission are equally k, the amplification factor of the non-modulated reception signal may be changed. That is, when the amplitude of the non-modulated reception signal is greater than the predetermined threshold value, the amplification factor of the non-modulated reception signal is set to G/k. In this case, the amplification factor of the modulated reception signal is assumed to be the set amplification factor G.

Also in the present embodiment, when all modulation coefficients of the modulated transmission are equally k, an amplification section having an amplification factor of k and an amplification section having an amplification factor of k*G may be separately provided so that switching between amplification sections to be used is performed according to the designated amplification factor.

As described above, according to the present embodiment, the detection section 340 that detects the amplitude of the echo of the non-modulated transmission is further provided. Then, when the amplitude detected by the detection section 340 is equal to or greater than the predetermined threshold value, the control unit 106 controls the amplification factor of the amplification section 310 in the same manner as in the first embodiment. For example, only when the non-modulated reception signal 512 exceeds the linear amplification range of the amplification section 310, the amplification factor of the amplification section 310 of the modulated reception signal 522 is changed. Therefore, waveform distortions after analog amplification of the respective reception signals that form one scanning line can be efficiently made to be approximately the same compared with the first embodiment. Therefore, the same effect as in the first embodiment can be efficiently obtained.

Third Embodiment

Next, a third embodiment to which the present invention is applied will be described. In the present embodiment, as in the second embodiment, when the amplitude of the non-modulated reception signal exceeds the linear amplification range of the amplification section 310, the amplification factor of the amplification section 310 is controlled. In the present embodiment, however, the amplitude of the reception signal amplified by changing the amplification factor is returned to the original amplitude before the input to the signal processing unit 104 thereafter. Then, the signal processing unit 104 performs the arithmetic processing 550 regardless of the magnitude of the amplitude of the non-modulated transmission.

Figure 8:
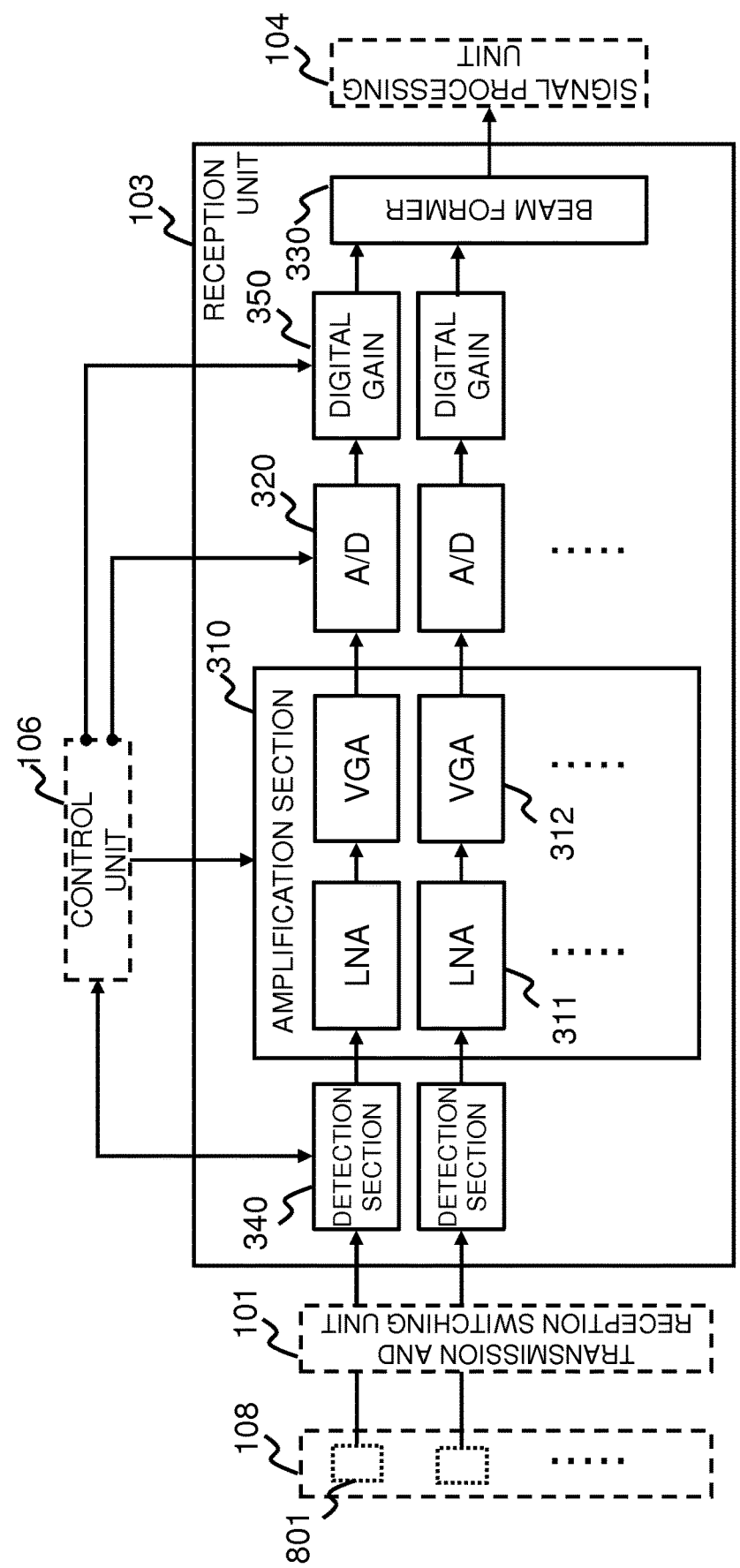
FIG. 8 is a block diagram of a reception unit of a third embodiment.

The configuration of the ultrasonic imaging apparatus 100 of the present embodiment is basically the same as that of the second embodiment. In the present embodiment, however, as described above, in the reception unit 103, the modulated reception signal is amplified by changing the amplification factor and is then returned to have the original amplitude. For this reason, as shown in FIG. 8, the reception unit 103 includes a digital gain 350, which digitally amplifies (attenuates) the reception signal after digital conversion (digital data), after the A/D conversion section 320.

The digital gain 350 is a circuit that linearly amplifies a signal of any amplitude with a desired amplification factor. For example, a signal that has caused electrical waveform distortion in the amplification section 310 maintains the distorted waveform even after the passage of the digital gain 350. In the present embodiment, the modulated reception signal after amplification in the amplification section 310 is returned to have the original amplitude according to the control signal from the control unit 106.

When a flag is set, that is, when the amplitude of the non-modulated reception signal exceeds a predetermined threshold value, the control unit 106 transmits a control signal instructing the change of the amplification factor not only to the amplification section 310 but also to the digital gain 350. For example, when the amplification factor of the amplification section 310 with respect to the echo (modulated reception signal) of the modulated transmission is increased k times, the control unit 106 controls the digital gain 350 to multiply the digital data obtained from the echo by 1/k. Thus, in the reception unit 103 of the present embodiment, amplified data obtained by increasing the amplification factor k times in the amplification section 310 is amplified to 1/k times in the digital gain 350, thereby being returned to the original data.

The energy relationship between the respective reception signals after passing through the digital gain 350 is the same as the energy relationship at the time of echo waves during the input to the reception unit 103. Therefore, regardless of whether or not the amplification factor has been changed in the amplification section 310, arithmetic processing in the subsequent arithmetic processing section 402 may be the arithmetic processing 550 described in the first embodiment, as in the related art. Therefore, the control unit 106 of the present embodiment transmits no control signal to the subsequent signal processing unit 104 regardless of the setting of the flag.

For example, the number of transmissions N is set to 2, the first transmission is set to non-modulated transmission, the second transmission is set to modulated transmission, and the modulation coefficient $k_2$ of the modulated transmission is set to 2. In this case, ratio of the energy of the waves of two transmission signals is 4:1. When the first reception signal is outside of the linear amplification range of the amplification section 310, the second reception signal is amplified with twice the amplification factor of the first reception signal by the amplification section 310. As a result, the energy of the first reception signal and the energy of the second reception signal become numerically the same, and the second reception signal becomes a signal waveform having the same electrical waveform distortion as the first reception signal.

The second reception signal amplified with the doubled amplification factor by the amplification section 310 is amplified to ½ times by the subsequent digital gain 350. Accordingly, only the amplitude of the second reception signal is reduced to ½ times while maintaining the distorted waveform. Therefore, the energy ratio between the two signals is 4:1 that is the same as at the time of transmission.

Assuming that the amplitude (signal strength) of the first reception signal finally obtained after beam forming is $S_1$ and the amplitude (signal strength) of the second reception signal finally obtained after beam forming is $S_2$, subsequent arithmetic processing in the arithmetic processing section 402 is the multiplication processing 551 and the subtraction processing 552, that is, $S_1-(k_2*S_2)$, that is, $S_1-2*S_2$, as in the related art.

For example, a case in which the number of transmissions N is 3, the first transmission is non-modulated transmission, the second and third transmissions are modulated transmissions, and a modulation coefficient $k_2$ of the second transmission and a modulation coefficient $k_3$ of the third transmission are 2 will be described as an example. When the first reception signal is outside of the linear amplification range of the amplification section 310, the control unit 106 doubles the amplification factor of the amplification section 310 with respect to the second and third reception signals. The energy of each reception signal after amplification is numerically the same.

The second and third reception signals amplified with the doubled amplification factor are amplified to ½ times by the subsequent digital gain 350. As a result, the energy ratio of the respective reception signals becomes the same as at the time of transmission. Assuming that the respective reception signals that are finally obtained after beam forming are $S_1$, $S_2$, and $S_3$, subsequent arithmetic processing in the arithmetic processing section 402 is the multiplication processing 551, average value calculation processing, and the subtraction processing 552, that is, $S_1-(k_2*S_2+k_3*S_3)/(3-1)$, that is, $S_1-(S_2+S_3)$, as in the related art.

Also in the present embodiment, when all modulation coefficients of the modulated transmission are equally (k), if the non-modulated reception signal is outside of the linear amplification range of the amplification section 310, the amplification factor of the non-modulated reception signal may be set to 1/k times, and may be set to k times in the digital gain 350. In this case, for the modulated reception signal, the amplification factor of the amplification section 310 is not changed, and amplification is not performed in the digital gain 350.

In the present embodiment, as shown in FIG. 8, the digital gain 350 is connected immediately after the A/D conversion section 320. Since the digital gain 350 is intended to change the amplitude of the reception signal after conversion into digital data, the digital gain 350 may be disposed anywhere in the reception unit 103 as long as the position is after the A/D conversion section 320. For example, the digital gain 350 may be disposed after the beam former 330.

Although the case of the combination with the second embodiment has been described as an example in the above explanation, the present invention is not limited thereto. Combination with the first embodiment is also possible. In this case, the control unit 106 transmits a control signal to the digital gain 350 during echo reception for all modulated transmissions. In addition, in the case of the combination with the first embodiment, the non-modulated transmission may not be the first transmission.

As described above, according to the present embodiment, the digital gain 350 that digitally amplifies the digital data is further provided. In addition, when the amplification factor of the amplification section 310 with respect to the echo of the modulated transmission is increased k (k is a real number) times, the control unit 106 controls the digital gain 350 to amplify the digital data obtained from the echo to 1/k times.

That is, according to the present embodiment, in the amplitude modulation method of the THI, the amplification factor at the time of analog amplification of the reception signal obtained from the echo of the ultrasonic beam is changed according to the amplitude of the transmitted ultrasonic beam. The change is performed so that the influence on the echo due to analog amplification is approximately the same between the respective echoes. When the amplification factor of the amplification section 310 is changed, returning to the original amplitude is performed in the digital gain 350.

Therefore, since the waveform distortion of the non-modulated reception signal after amplification becomes approximately the same as the waveform distortion of the modulated reception signal after amplification, the amplitude ratio of both the non-modulated reception signal and the modulated reception signal after analog amplification is the same as that assumed. Based on this, it is possible to correctly perform subsequent arithmetic processing. In this case, in the present embodiment, the amplitude ratio of both signals before arithmetic processing is 1/k as in the related art. For this reason, in the present embodiment, the conventional arithmetic processing section can be used as it is for arithmetic processing in the signal processing unit 104. Therefore, according to the present embodiment, it is possible to obtain the same effect as in the first or second embodiment without changing the signal processing unit 104.

Fourth Embodiment

Next, a fourth embodiment to which the present invention is applied will be described. Also in the present embodiment, as in the first to third embodiments, the influence on the echo due to analog amplification is made to be the same among reception signals by controlling the amplification factor of the amplification section. However, although the arithmetic processing is performed after the beam forming of data for each channel in each of the embodiments described above, the arithmetic processing is performed before the beam forming for the data of each channel in the present embodiment.

The ultrasonic imaging apparatus 100 of the present embodiment has basically the same configuration as in the first embodiment. However, the configuration of the reception unit 103 and the signal processing unit 104, the processing of the beam former 330, and the processing of the control unit 106 that controls these are different. Hereinafter, the present embodiment will be described focusing on the different configuration from the first embodiment.

Figure 9:
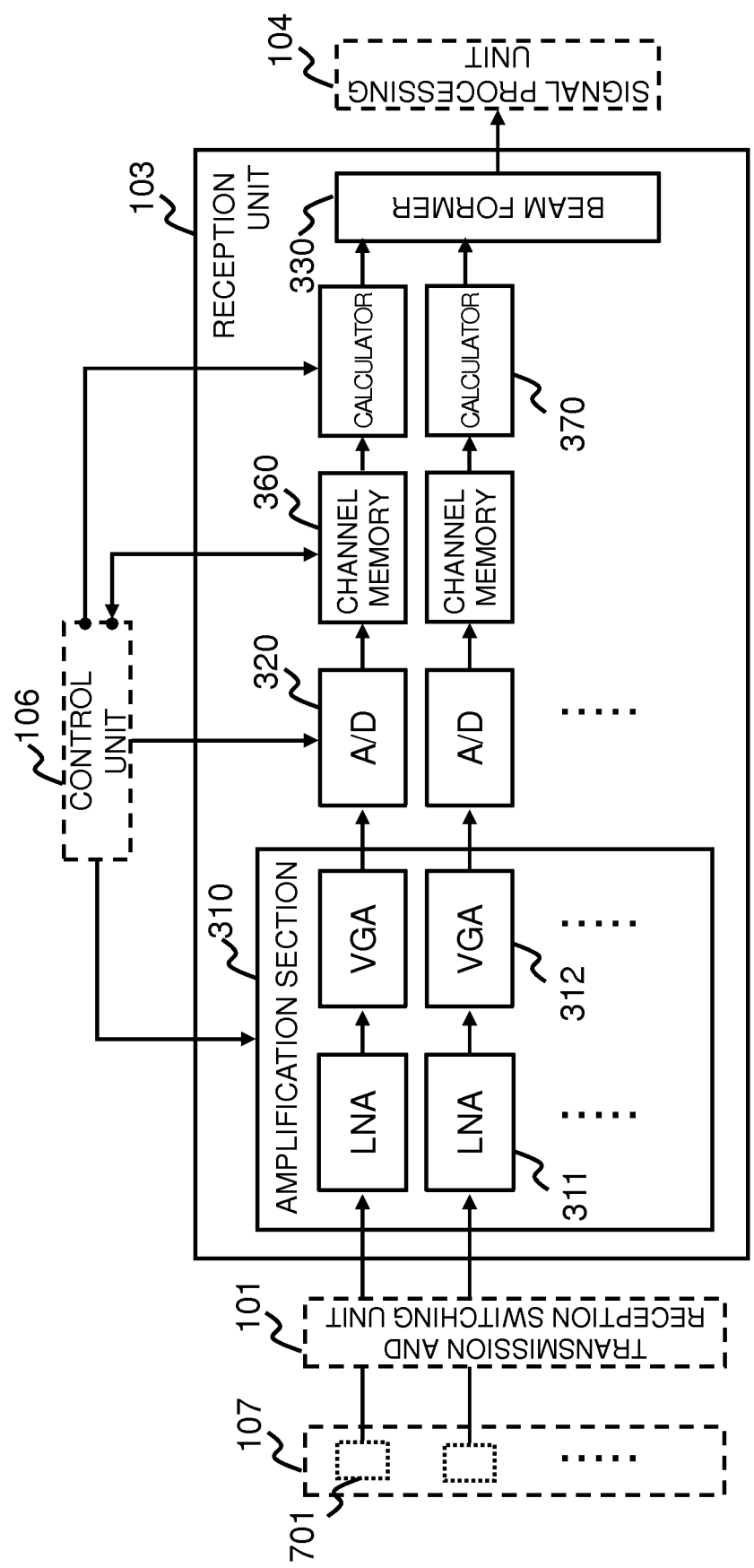
FIG. 9 is a block diagram of a reception unit of a fourth embodiment.

As shown in FIG. 9, the reception unit 103 of the present embodiment further includes a channel memory 360, in which a reception signal (digital data) after conversion in the A/D conversion section 320 is stored for each channel, and a calculator 370 that extracts a nonlinear component for each channel by performing arithmetic processing on the digital data stored in the channel memory 360.

The channel memory 360 is connected after the A/D conversion section 320, and digital data converted from each reception signal in N receptions is stored for each channel.

The calculator 370 is connected after the channel memory 360, and performs arithmetic processing for each channel using the digital data of each channel memory 360 after N receptions. Here, according to the control signal from the control unit 106, the average value calculation processing and the above-described subtraction processing 552 described above are performed.

The beam former 330 of the present embodiment performs beam forming of the data after arithmetic processing. That is, beam forming of the extracted nonlinear component for each channel is performed. Then, the image processing unit 107 of the present embodiment constructs an image using the beam forming result.

In addition, the signal processing unit 104 of the present embodiment does not need to include the arithmetic processing section 402 since the calculator 370 performs arithmetic processing.

Also in the present embodiment, as in the first embodiment, the amplification factor of the non-modulated reception signal may be changed. In addition, an amplifier may be provided for each amplification factor.

Also in the present embodiment, as in the second embodiment, the detection section 340 may be provided before the amplification section 310, and the amplification factor of the modulated transmission and reception signals may be changed only when the amplitude of the non-modulated reception signal exceeds the linear amplification range of the amplification section 310.

In this case, when changing the amplification factor, the control unit 106 also transmits a control signal to the calculator 370. In response to the control signal, the calculator 370 performs not only the average value calculation processing and the subtraction processing 552 described above but also the multiplication processing 551 on the data for each channel.

In addition, as in the third embodiment, a signal amplified by changing the amplification factor may be processed to have the original amplitude before arithmetic processing. In this case, in the calculator 370, the same arithmetic processing as in the related art is performed for any signal.

As described above, according to the present embodiment, there are provided the channel memory 360 in which the digital data after conversion in the digital conversion section 320 is stored for each channel, the calculator 370 that extracts the nonlinear component for each channel by performing arithmetic processing on the digital data stored in the channel memory 360, and the beam former 330 that performs beam forming of the extracted nonlinear component for each channel.

That is, according to the present embodiment, in the amplitude modulation method of the THI, the amplification factor at the time of analog amplification of the reception signal obtained from the echo of the ultrasonic beam is changed according to the amplitude of the transmitted ultrasonic beam. The change is performed so that the influence on the echo due to analog amplification is approximately the same between the respective echoes. Then, a nonlinear component is extracted for each channel.

Therefore, since the waveform distortion of the non-modulated reception signal after amplification becomes approximately the same as the waveform distortion of the modulated reception signal after amplification, the amplitude ratio of both the non-modulated reception signal and the modulated reception signal after analog amplification is the same as that assumed. Based on this, it is possible to correctly perform subsequent arithmetic processing. In this case, in the present embodiment, since the digital data before beam forming is already a nonlinear component, it is sufficient to perform the beam forming processing for creating the image data of the imaging region set in advance only once. Therefore, according to the present embodiment, it is possible to extract a nonlinear component with high accuracy, in the same manner as in the first embodiment, by one beam forming processing without performing beam forming processing for each transmission. As a result, the obtained image quality is also improved.

Fifth Embodiment

Next, a fifth embodiment to which the present invention is applied will be described. In the present embodiment, the influence of electrical distortion of the signal waveform received in the amplification section 310 formed by an analog amplifier is made to be approximately the same for all reception signals by using a filter. The present embodiment is based on the assumption that the input and output characteristics of the amplification section 310 are known.

The ultrasonic imaging apparatus 100 of the present embodiment has basically the same configuration as in the first embodiment. However, the configuration of the reception unit 103 is different, and the processing of the control unit 106 that controls these is different. Hereinafter, the present embodiment will be described focusing on the different configuration from the first embodiment.

Figure 10:
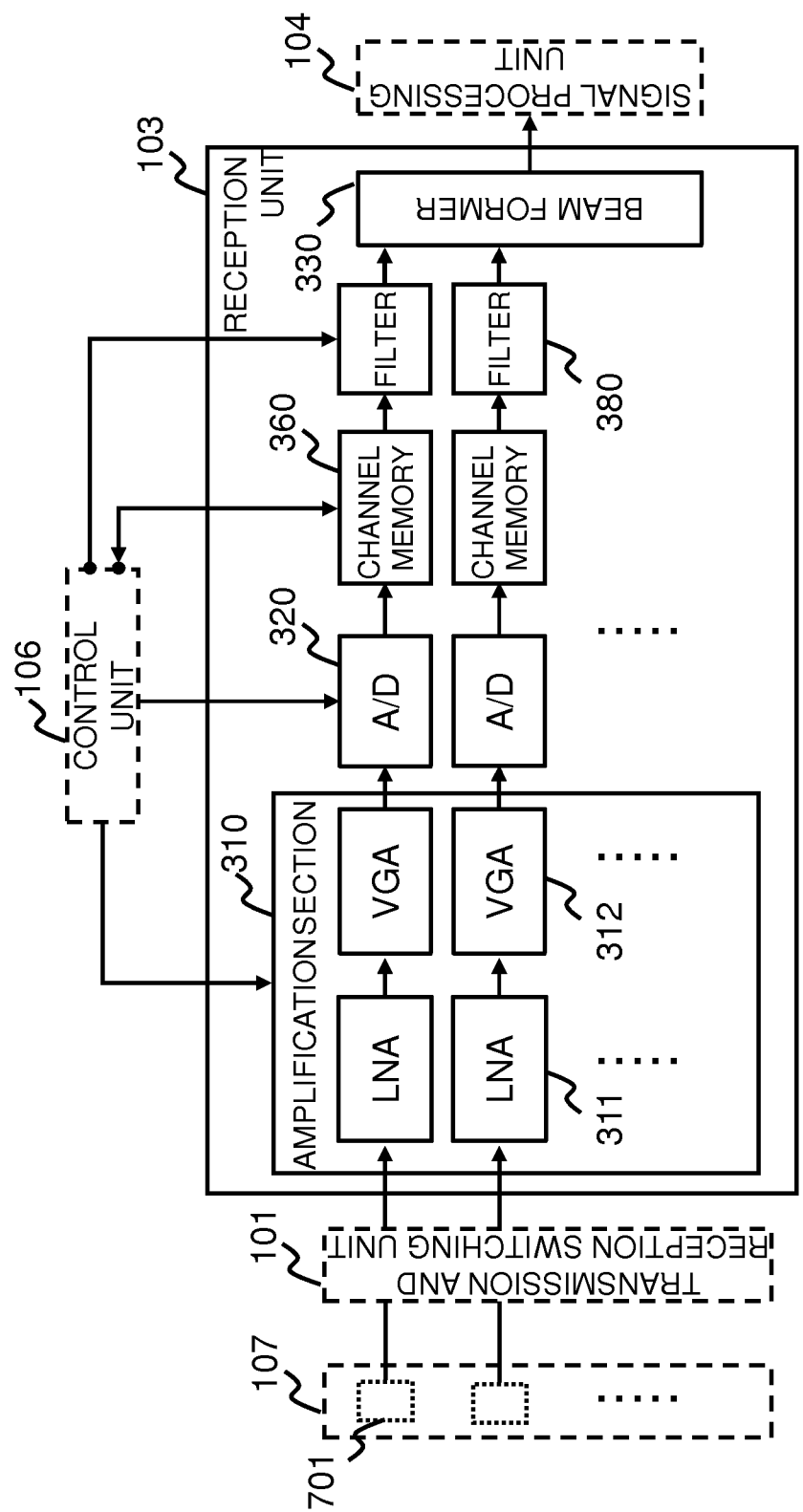
FIG. 10 is a block diagram of a reception unit of a fifth embodiment.

As shown in FIG. 10, the reception unit 103 of the present embodiment further includes a channel memory 360, in which digital data converted by the A/D conversion section 320 is stored for each channel, and a filter 380 that performs filtering processing on the digital data.

In the same manner as in the conventional ultrasonic imaging apparatus, the amplification section 310 of the present embodiment amplifies a non-modulated reception signal and a modulated reception signal with an amplification factor (set amplification factor) G set in advance. Unlike the amplification section 310 of the ultrasonic imaging apparatus 100 of the first embodiment, the amplification factor is not changed according to the modulated reception signal and the non-modulated reception signal.

As in the fourth embodiment, the channel memory 360 is connected after the A/D conversion section 320, and digital data converted from each of reception signals that are received N times is stored for each channel.

The filter 380 of the present embodiment has approximately the same transfer function as the input and output characteristics of the amplification section 310. That is, the waveform after passing through the filter 380 shows approximately the same electrical distortion as after passing through the amplification section 310. Therefore, the filtering processing of the filter 380 of the present embodiment is processing for giving the same waveform distortion as electrical distortion that the non-modulated reception signal receives to the modulated reception signal. The filter 380 of the present embodiment reads data from the channel memory 360 after all transmissions are completed, and performs this filtering processing on the digital data obtained from the modulated reception signal. The filtering processing of the filter 380 is performed according to the control signal from the control unit 106.

The beam former 330 of the present embodiment performs beam forming processing on the digital data for each channel after the filtering processing. Then, the signal processing unit 104 of the present embodiment performs the same arithmetic processing as in the first embodiment for the reception beam after the beam forming. That is, the average value calculation processing and the subtraction processing 552 are performed to extract a nonlinear component. Then, the image processing unit 107 of the present embodiment constructs an image from the nonlinear component extracted by the signal processing unit 104.

Although the filter 380 of the present embodiment performs processing for giving distortion to the digital data obtained from the modulated reception signal, the present invention is not limited thereto. A filter having a characteristic of restoring the electrical distortion that the non-modulated reception signal receives due to the amplification section 310 may also be used. In this case, the filtering processing is performed on the digital data obtained from the non-modulated reception signal, among the data of the channel memory 360, so as to correct the electrical distortion that the reception signal receives.

In addition, the position of the filter 380 is not limited to the above-described position. For example, the filter 380 may be disposed immediately after the A/D conversion section 320. In the case of reception in which filtering processing is performed, among N receptions, the control unit 106 transmits a control signal instructing to perform filtering processing to the filter 380. In addition, when it is determined whether or not filtering processing is performed for each reception, the channel memory 360 may be disposed or may not.

The filter 380 of the present embodiment may also be provided in the signal processing unit 104. In this case, in the reception beam after beam forming, electrical distortion received due to analog amplification is adjusted. As described above, the adjustment is performed on the reception beam generated from each reception signal so that the electrical distortion received by the non-modulated reception signal is approximately the same as the electrical distortion received by the modulated reception signal.

In this case, the configuration of the reception unit 103 is the amplification section 310, the A/D conversion section 320, and the beam former 330.

Also in the present embodiment, the detection section 340 may be provided before the amplification section 310, and filtering processing may be performed by the filter 380 only when the amplitude of the non-modulated echo signal exceeds the linear amplification range of the amplification section 310.

In this case, according to the detection result of the detection section 340, the control unit 106 transmits a control signal to the filter 380. That is, when the amplitude of the non-modulated reception signal is equal to or greater than the predetermined threshold value, the detection section 340 transmits a control signal to the filter 380 so as to perform filtering processing on the modulated reception signal. Alternatively, a control signal is transmitted to the filter 380 so that the waveform of the non-modulated reception signal is restored.

Also in the present embodiment, the calculator 370 may be provided before the beam former 330 so that arithmetic processing is performed before beam forming. In this case, the calculator 370 is disposed after the filter 380. In addition, in this case, the signal processing unit 104 may not be provided.

As described above, according to the present embodiment, the filter 380 that performs filtering processing on the digital data after conversion in the A/D conversion section 320 is provided, and the control unit 106 makes the influence on the echo due to analog amplification approximately the same by controlling the execution of filtering. For example, the filter 380 is made to execute filtering processing on the digital data obtained from the echo of the modulated transmission. The filter 380 is assumed to have approximately the same transfer function as electrical distortion due to analog amplification.

That is, according to the present embodiment, the influence due to an analog circuit is made to be approximately the same for the echoes of multiple transmissions in the amplitude modulation method of the THI by correcting the waveform with the filter 380. For the correction of the waveform, the same distortion as electrical distortion that the non-modulated reception signal receives from the analog circuit is given to the modulated reception signal, or electrical distortion that the non-modulated reception signal receives is restored. Therefore, since the waveform distortion of the non-modulated reception signal after amplification becomes approximately the same as the waveform distortion of the modulated reception signal after amplification, the amplitude ratio of both the non-modulated reception signal and the modulated reception signal after analog amplification is the same as that assumed. Based on this, it is possible to correctly perform subsequent arithmetic processing. Therefore, since it is possible to extract a nonlinear component with high accuracy, the obtained image quality is also improved.

In addition, according to the present embodiment, since the electrical distortion is corrected by the filter 380 as described above, the same effect as in the first embodiment can be obtained with a simpler configuration.

In each of the embodiments described above, at the time of modulated transmission, sound pressure modulation is realized by multiplying the amplitude of the transmission waveform of the transmission beam by 1/k in the transmission unit. However, the method for realizing the modulation is not limited thereto. For example, by using the fact that the transmitted sound pressure is proportional to the area within the ultrasonic transmission and reception surface, the modulation is realized by changing the area.

The area is determined by the number of channels 801 to be driven in the ultrasonic probe 108. Therefore, the sound pressure (amplitude) of all transmission beams is adjusted by changing the number of channels to be driven (the number of electro-acoustic elements to be driven). In this case, the waveforms of transmission signals input to the respective electro-acoustic transducer elements are assumed to be the same.

Specifically, the transmission unit 102 generates an ultrasonic beam by driving multiple electro-acoustic transducer elements provided in the ultrasonic probe 108. In this case, the control unit 106 drives all electro-acoustic elements having a predetermined area, among the multiple electro-acoustic transducer elements, at the time of non-modulated transmission, and selectively drives only some of the electro-acoustic transducer elements having a predetermined area in units of a channel at the time of modulated transmission.

Figure 11A:
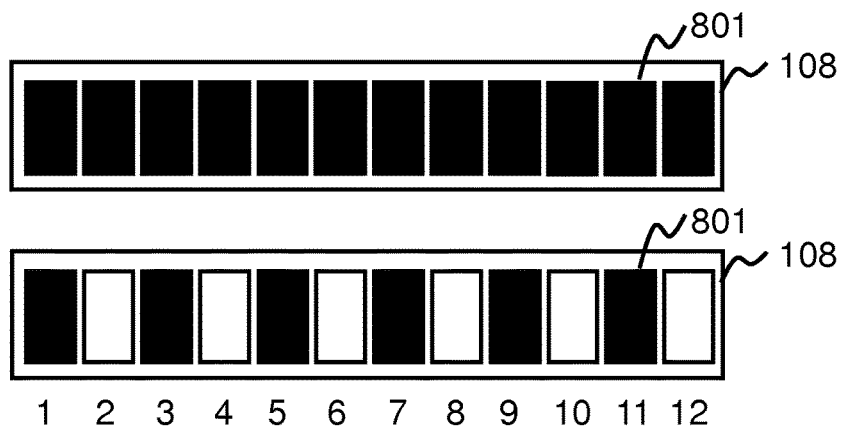
FIG. 11A is a diagram for explaining other amplitude modulation methods of the embodiment of the present invention.
Figure 11B:
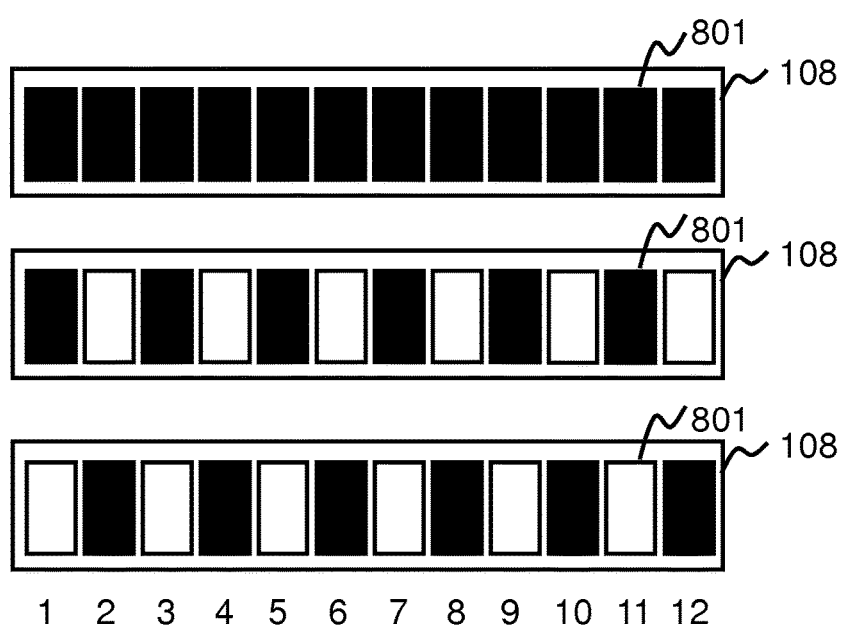
FIG. 11B is a diagram for explaining other amplitude modulation methods of the embodiment of the present invention.

That is, a driving area on the ultrasonic transmission and reception surface at the time of modulated transmission is made to be smaller than that at the time of non-modulated transmission. For example, when the number of transmissions N is 2, as shown in FIG. 11A, all channels 801 in the aperture are driven at the time of non-modulated transmission (in the first transmission). On the other hand, at the time of modulated transmission (in the second transmission), the channels 801 of the half at the time of non-modulated transmission are driven. In FIGS. 11A and 11B, black channels 801 are driving channels. In this case, the arrangement of channels to be driven does not matter. In this manner, it is possible to transmit the ultrasonic beam of the half of sound pressure at the time of modulated transmission.

That is, when the number of modulated transmissions is 1, at the time of modulated transmission, the half of electro-acoustic transducer elements driven at the time of non-modulated transmission is driven.

For example, FIG. 11B shows driving channels at the time of each transmission when the number of transmissions N is 3. Here, a serial number is given to each channel 801 from the end. As shown in this diagram, at the time of non-modulated transmission (in the first transmission), all channels in the aperture are driven. On the other hand, in two modulated transmissions, odd-numbered channels 801 are driven at the time of first modulated transmission (in the second transmission), and even-numbered channels 801 are driven at the time of the other modulated transmission (in the third transmission).

When the odd-numbered channels are driven, the channel pitch becomes larger than the wavelength of the transmission pulse. For this reason, a grating lobe having directivity in a direction different from the main axis may be generated. The grating lobe can be reduced by driving the even-numbered channels in the third transmission as described above.

That is, when the number of modulated transmissions is 2 times or more, electro-acoustic transducer elements that are selected at the time of two or more modulated transmissions are exclusively selected among the respective transmissions from electro-acoustic transducer elements driven at the time of non-modulated transmission.

In addition to the case in which electro-acoustic transducer elements that are located exclusively as described above are temporally selected as driving channels (when selected at different transmission timings), the same effect is obtained even when the electro-acoustic transducer elements that are located exclusively are spatially selected.

Figure 11C:
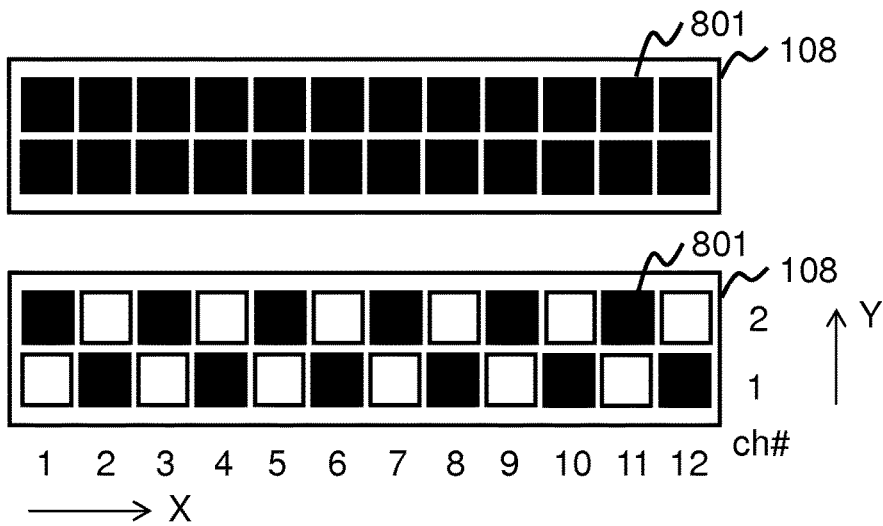
FIG. 11C is a diagram for explaining other amplitude modulation methods of the embodiment of the present invention.

As shown in FIG. 11C, assuming that an array direction of inputting a signal under delay control for forming an ultrasonic beam is X and a direction perpendicular to the X direction is Y, driving channels are located exclusively in the Y-direction array.

For example, FIG. 11C shows a case in which channels are arranged in a two-dimensional manner. At the time of non-modulated transmission (in the first transmission), all channels 801 in the aperture are driven. At the time of modulated transmission (in the second transmission), the channels 801 of the half at the time of non-modulated transmission are driven.

Specifically, when viewed for ch#1 in the X direction, ch#2 in the Y direction is driven. When viewed for ch#2 in the X direction, ch#1 in the Y direction is driven. Thus, in the X-direction array, ch#1 or ch#2 in the Y direction is driven.

Although the total number of driving channels in the second transmission is ½ of that in the first transmission, the number of driving channel in the X-direction array is the same as that in the first transmission. In this case, the number of transmissions N can be reduced from N>2 to N=2.

In addition, if the same transmission aperture as when all channels are driven is applied for the X direction, channels in the Y direction may be driven any number of times. Therefore, when there is a further increase in the array in the Y direction, it is possible to adopt a configuration in which a driving channel pattern as in the second transmission of FIG. 11C is repeatedly arranged.

When modulation is realized by changing the driving area, ideal THI can be performed even in the following cases. That is, this is a case in which the electro-acoustic transducer element responds nonlinearly to the voltage of the transmission signal and accordingly it is difficult to modulate only the amplitude while maintaining the waveform of the transmission pulse. Also in such a case, since the waveform of the supplied transmission signal is the same in each electro-acoustic transducer element regardless of non-modulated transmission and modulated transmission, it is possible to transmit the transmission pulse that is not affected by the nonlinearity of the electro-acoustic element. As a result, it is possible to reduce the sound pressure of the ultrasonic beam.

REFERENCE SIGNS LIST

100: ultrasonic imaging apparatus
101: transmission and reception switching unit
102: transmission unit
103: reception unit
104: signal processing unit
105: reception processing unit
106: control unit
107: image processing unit
108: ultrasonic probe
120: imaging target
121: user interface
122: display unit
310: amplification section
311: LNA
312: VGA
320: A/D conversion section
330: beam former
340: detection section
350: digital gain
360: channel memory
370: calculator
380: filter
401: memory
402: arithmetic processing section
403: filtering section
511: transmission signal 512: non-modulated reception signal
512a: fundamental wave band component
512b: nonlinear component
521: transmission signal
522: modulated reception signal
522a: fundamental wave band component
522b: nonlinear component
523: signal
523a: fundamental wave band component
523b: nonlinear component
540a: difference between fundamental wave band components
540b: difference between nonlinear components
550: arithmetic processing
551: multiplication processing
552: subtraction processing
801: channel

The invention claimed is:

1. An ultrasonic imaging apparatus, comprising:
a transmission unit that transmits an ultrasonic beam multiple times to a predetermined position of an imaging target through an ultrasonic probe;
a reception processing unit that receives an echo of the ultrasonic beam from the imaging target through the ultrasonic probe in a channel unit set in advance and extracts a nonlinear component after analog amplification;
an image processing unit that constructs an image of the imaging target using the nonlinear component; and
a control unit that controls the reception processing unit and the transmission unit,
wherein the multiple transmissions include one non-modulated transmission in which the ultrasonic beam is transmitted with a predetermined set amplitude that is not modulated,
wherein the reception processing unit, having been controlled by the control unit such that an influence on an echo due to the analog amplification is the same between an echo of the non-modulated transmission and an echo of modulated transmission that is a transmission other than the non-modulated transmission, extracts the nonlinear component after analog amplification with the same influence between the echo of the non-modulated transmission and the echo of the modulated transmission,
wherein a modulation reception signal is obtained from the echo of the modulated transmission and a non-modulation reception signal is obtained from the echo of the non-modulation transmission,
wherein the reception processing unit includes an analog-to-digital conversion section that obtains digital data by digitally converting the echo after the analog amplification and a filter that performs filtering processing on the digital data,
wherein the filter has the same transfer function as electrical distortion that the non-modulation reception signal receives due to the analog amplification, and
wherein the control unit makes the influence on the echo due to the analog amplification the same by controlling execution of the filtering processing to give a waveform distortion that is same as the electrical distortion that the non-modulation reception signal receives to the modulated reception signal.

2. The ultrasonic imaging apparatus according to claim 1, wherein the control unit causes the filter to execute the filtering processing on digital data obtained from the echo of the modulated transmission.

3. The ultrasonic imaging apparatus according to claim 1, wherein the reception processing unit includes an analog-to-digital conversion section that converts the echo after the analog amplification into digital data, a beam former that performs beam forming of digital data for each channel to obtain a reception beam, and a signal processing section that performs arithmetic processing on the reception beam to extract the nonlinear component.

4. The ultrasonic imaging apparatus according to claim 1, wherein the reception processing unit includes an analog-to-digital conversion section that converts the echo after the analog amplification into digital data, a channel memory in which the digital data is stored for each channel, a calculator that extracts the nonlinear component for each channel by performing arithmetic processing on the digital data stored in the channel memory, and a beam former that performs beam forming of the extracted nonlinear component for each channel.

5. The ultrasonic imaging apparatus according to claim 1, wherein the reception processing unit further includes a channel memory in which the digital data is stored for each channel, a beam former that performs beam forming of digital data after the filtering processing to obtain a reception beam, and a signal processing section that performs arithmetic processing on the reception beam to extract the nonlinear component.

6. The ultrasonic imaging apparatus according to claim 1, wherein the transmission unit generates the ultrasonic beam by driving multiple electro-acoustic transducer elements provided in the ultrasonic probe, and
the control unit controls the transmission unit such that all electro-acoustic transducer elements having a predetermined area within an ultrasonic transmission and reception surface of the ultrasonic imaging apparatus, among the multiple of electro-acoustic transducer elements, are driven at the time of the non-modulated transmission and only some of the electro-acoustic transducer elements having the predetermined area are selectively driven in the channel unit at the time of the modulated transmission.

7. The ultrasonic imaging apparatus according to claim 6, wherein the number of times of the modulated transmission is 1, and
at the time of the modulated transmission, a half of electro-acoustic transducer elements driven at the time of the non-modulated transmission is driven.

8. The ultrasonic imaging apparatus according to claim 6, wherein the number of times of the modulated transmission is 2, and
the electro-acoustic transducer elements selected at the time of the two modulated transmissions are exclusively selected between respective transmissions from electro-acoustic transducer elements driven at the time of the non-modulated transmission.

9. The ultrasonic imaging apparatus according to claim 1, wherein the reception processing unit extracts the nonlinear component by calculating an average value of digital data obtained from the echo of the modulated transmission after performing amplification with a predetermined modulation coefficient and subtracting the obtained value from digital data obtained from the echo of the non-modulated transmission, and
the predetermined modulation coefficient is an inverse of a ratio of an amplitude of an ultrasonic beam of the modulated transmission to the set amplitude.

10. An ultrasonic imaging method, comprising:
obtaining echoes by performing one non-modulated transmission for transmitting an ultrasonic beam to a predetermined position of an imaging target with a set amplitude that is set in advance without modulation and one or more modulated transmissions for transmitting the ultrasonic beam with an amplitude obtained by modulating the set amplitude, wherein a modulation reception signal is obtained from the echo of the modulated transmission and a non-modulation reception signal is obtained from the echo of the non-modulation transmission;
making an influence of electrical distortion due to analog amplification the same between the echo of the non-modulated transmission and the echo of the modulated transmission;
extracting a nonlinear component after analog amplification with the same influence between the echo of the non-modulated transmission and the echo of the modulated transmission;
constructing an image of the imaging target from the extracted nonlinear component;
obtaining digital data by digitally converting the echo after the analog amplification and performing filtering processing on the digital data using a filter, the filter having the same transfer function as electrical distortion that the non-modulation reception signal receives due to the analog amplification; and
making the influence due to the analog amplification the same between the echo of the non-modulated transmission and the echo of the modulated transmission by controlling execution of the filtering processing to give a waveform distortion that is same as the electrical distortion that the non-modulation reception signal receives to the modulated reception signal.

11. The ultrasonic imaging method according to claim 10, further comprising:
causing the filter to execute the filtering processing on digital data obtained from the echo of the modulated transmission.

12. The ultrasonic imaging method according to claim 10, further comprising:
generating the ultrasonic beam by driving multiple electro-acoustic transducer elements provided in the ultrasonic probe; and
controlling the transmission unit such that all electro-acoustic transducer elements having a predetermined area within an ultrasonic transmission and reception surface of the ultrasonic imaging apparatus, among the multiple of electro-acoustic transducer elements, are driven at the time of the non-modulated transmission and only some of the electro-acoustic transducer elements having the predetermined area are selectively driven in the channel unit at the time of the modulated transmission.

13. The ultrasonic imaging method according to claim 12, wherein the number of times of the modulated transmission is 1, and at the time of the modulated transmission, a half of electro-acoustic transducer elements driven at the time of the non-modulated transmission is driven.

14. The ultrasonic imaging apparatus according to claim 12, wherein the number of times of the modulated transmission is 2, and
the electro-acoustic transducer elements selected at the time of the two modulated transmissions are exclusively selected between respective transmissions from electro-acoustic transducer elements driven at the time of the non-modulated transmission.

* * * * *